(12) United States Patent
Norton et al.

(10) Patent No.: US 7,857,844 B2
(45) Date of Patent: *Dec. 28, 2010

(54) ATRAUMATIC STENT WITH REDUCED DEPLOYMENT FORCE, METHOD FOR MAKING THE SAME AND METHOD AND APPARATUS FOR DEPLOYING AND POSITIONING THE STENT

(75) Inventors: Paul K. Norton, Lunenburg, MA (US); Michael Zupkofska, Rockland, MA (US); Peter Brady, Galway (IE); Gary L. Leanna, Holden, MA (US); Claude O. Clerc, Marlborough, MA (US); William Bertolino, Framingham, MA (US); Grainne Hanley, Galway (IE)

(73) Assignee: Boston Scientific Scimed Inc., Maple Grove, MN (US)

( * ) Notice: Subject to any disclaimer, the term of this patent is extended or adjusted under 35 U.S.C. 154(b) by 54 days.

This patent is subject to a terminal disclaimer.

(21) Appl. No.: 12/261,474

(22) Filed: Oct. 30, 2008

(65) Prior Publication Data

US 2009/0054972 A1 Feb. 26, 2009

Related U.S. Application Data

(63) Continuation of application No. 11/271,774, filed on Nov. 10, 2005, now Pat. No. 7,462,192.

(60) Provisional application No. 60/626,729, filed on Nov. 10, 2004, provisional application No. 60/680,630, filed on May 13, 2005.

(51) Int. Cl.
*A61F 2/06* (2006.01)

(52) U.S. Cl. .................................................. 623/1.53
(58) Field of Classification Search ........ 623/1.15–1.54
See application file for complete search history.

(56) References Cited

U.S. PATENT DOCUMENTS

| 4,655,771 A | 4/1987 | Wallsten |
| 5,445,646 A | 8/1995 | Euteneuer et al. |
| 5,630,840 A | 5/1997 | Mayer |

(Continued)

FOREIGN PATENT DOCUMENTS

WO　　WO 93/19803　　10/1993

(Continued)

*Primary Examiner*—Suzette J Gherbi
(74) *Attorney, Agent, or Firm*—Hoffman & Baron, LLP

(57) ABSTRACT

An implantable stent includes a plurality of elongate wires braided to form a hollow tubular structure having a tubular wall to define an interior surface and an exterior surface and having opposed open first and second ends, wherein the opposed open first and second ends are atraumatic ends The atraumatic ends of the stent are desirably free of any loose wire ends. The wires include composite wires to enhance visibility of the wires to provide improved external imaging of the wires in the body. The elongate composite wires of the stent may be metallic wires having an outer metallic portion including a first metal, such as nitinol, and an inner metallic core portion including a second metal, which is a radiopaque material, such as gold, barium sulfate, ferritic particles, platinum, platinum-tungsten, palladium, platinum-iridium, rhodium, tantalum or combinations thereof.

20 Claims, 11 Drawing Sheets

U.S. PATENT DOCUMENTS

| | | | |
|---|---|---|---|
| 5,957,974 | A | 9/1999 | Thompson et al. |
| 6,241,757 | B1 * | 6/2001 | An et al. .................. 623/1.1 |
| 6,641,608 | B1 | 11/2003 | Pulnev |
| 7,001,425 | B2 * | 2/2006 | McCullagh et al. ........ 623/1.53 |
| 7,462,192 | B2 * | 12/2008 | Norton et al. .............. 623/1.53 |
| 7,655,039 | B2 * | 2/2010 | Leanna et al. ............. 623/1.53 |
| 2002/0035396 | A1 | 3/2002 | Heath |
| 2003/0153973 | A1 * | 8/2003 | Soun et al. ................ 623/1.16 |
| 2004/0039435 | A1 * | 2/2004 | Hancock et al. ............ 623/1.2 |
| 2004/0098099 | A1 | 5/2004 | McCullagh et al. |
| 2004/0186549 | A1 | 9/2004 | Jayaraman |
| 2005/0049682 | A1 | 3/2005 | Leanna et al. |
| 2006/0190075 | A1 * | 8/2006 | Jordan et al. ............. 623/1.23 |
| 2008/0300673 | A1 * | 12/2008 | Clerc et al. ................ 623/1.15 |

FOREIGN PATENT DOCUMENTS

| | | |
|---|---|---|
| WO | WO 2004/105647 | 12/2004 |
| WO | WO 2005/110286 | 11/2005 |

* cited by examiner

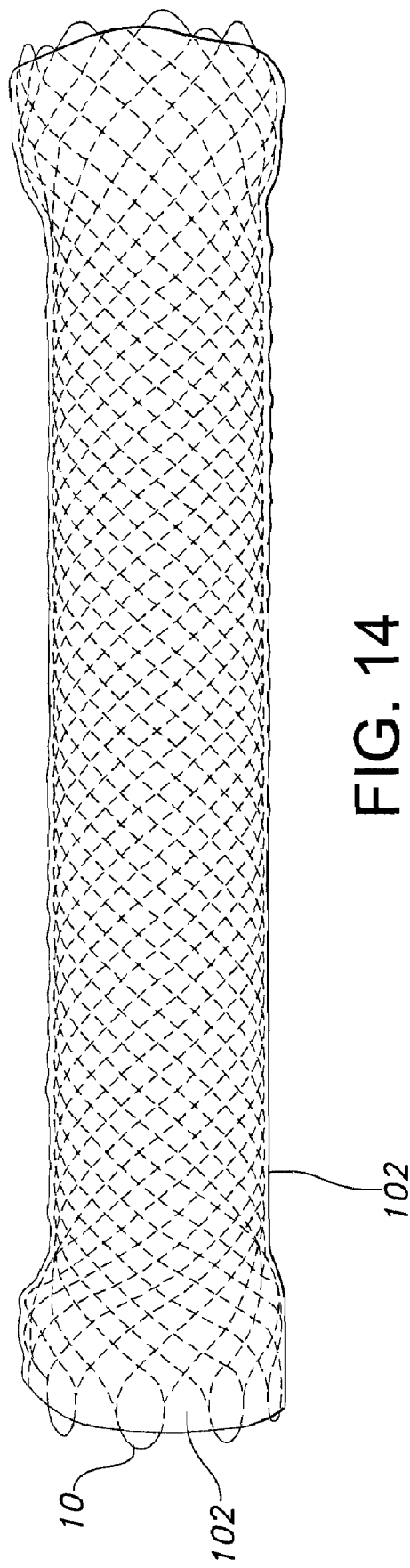
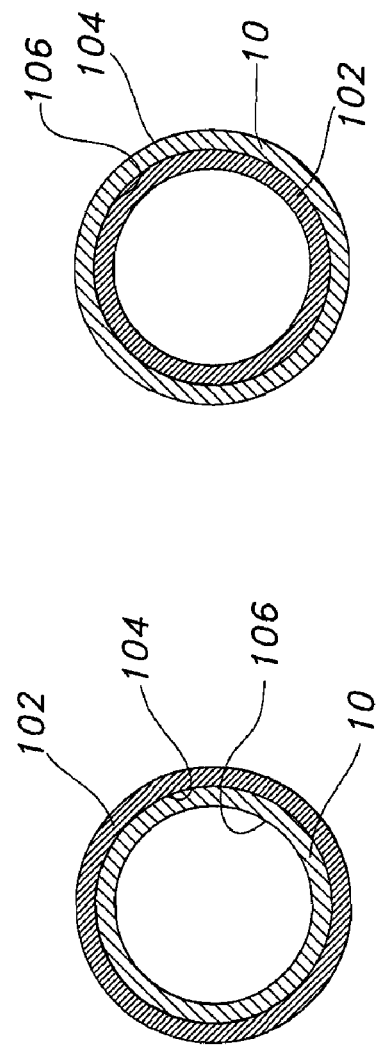
FIG. 14
FIG. 15
FIG. 16

US 7,857,844 B2

ATRAUMATIC STENT WITH REDUCED DEPLOYMENT FORCE, METHOD FOR MAKING THE SAME AND METHOD AND APPARATUS FOR DEPLOYING AND POSITIONING THE STENT

CROSS-REFERENCE TO RELATED APPLICATIONS

This application is a continuation of U.S. application Ser. No. 11/271,774, filed Nov. 10, 2005, which claims the benefit of U.S. Provisional Application No. 60/626,729, filed Nov. 10, 2004, and U.S. Provisional Application No. 60/680,630, filed May 13, 2005, the contents of all of which are incorporated herein by reference.

FIELD OF THE INVENTION

The present invention relates to a stent having atraumatic looped ends with smooth stent wire ends and improved stent wire welds. The present invention also relates to an apparatus for deploying and positioning the atraumatic stent.

BACKGROUND OF THE INVENTION

Stents made from interconnecting, often braiding, elongate wires may be made less traumatic, i.e., atraumatic, by closing the loose wire ends at the ends of the stents. The loose wire ends have typically been closed by mechanical means, for example by welding. Such mechanical means, however, often have sharp ends which may score the inside of a delivery system from which it is deployed or may also irritate bodily vessels or lumens in which the stent is placed. Further, the welds of prior art stent devices may fatigue over time leading to undesirable failure.

Thus, there is a need in the art for a stent made from elongate wires in a closed-end design while avoiding the disadvantages of the prior art. More particularly, there is a need in the art for improved stent welds and less traumatic welded stent wire ends.

SUMMARY OF THE INVENTION

In one aspect of the present invention, an implantable stent is provided. The stent includes a plurality of elongate wires braided to form a hollow tubular structure having a tubular wall to define an interior surface and an exterior surface and having opposed open first and second ends, wherein the opposed open first and second ends are atraumatic ends, and further wherein the wires include composite wires to enhance visibility of the wires to provide improved external imaging of the wires in the body. Desirably, the enhanced visibility is enhanced radiopacity and the external imaging is fluoroscopic or x-ray visualization.

The atraumatic ends of the stent are desirably free of any loose wire ends.

The elongate composite wires of the stent may be metallic wires having an outer metallic portion including a first metal and an inner metallic core portion including a second metal, wherein the first metal is different from the second metal. Desirably, the second metal of the inner core includes a radiopaque material selected from gold, barium sulfate, ferritic particles, platinum, platinum-tungsten, palladium, platinum-iridium, rhodium, tantalum or combinations thereof. The first metal of the outer portion may include nitinol.

The stent of this aspect of the present invention desirably may also have wires that terminate at the second end, wherein the wires at the first end are arranged in a series of closed loops with each loop having an apex defined by a bend in one of the wires and having an opposed base defined by crossing of adjacent wires, and further wherein the apex of adjacent closed loops are longitudinally offset from one and the other.

The stent of this aspect of the present invention desirably may also have wires that terminate at the second open end, and adjacently juxtaposed wires are securably joined at the second open end to provide first securably joined regions, wherein at least one of the adjacently juxtaposed stent wires are extended past the first securably joined regions and further wherein the extended and looped wire is securably joined to the proximal pair of wires with second securably joined regions to define closed loop wire ends. Desirably, the wires are securably joined by welding the wired and further wherein the securably joined regions are welds.

The stent of this aspect of the present invention desirably may also have wires that terminate at the second open end, and further wherein adjacently juxtaposed wires at the second open end are securably joined to provide securably joined regions, wherein ends of the terminated wires are smoothed to remove sharp edges from the wire ends. Desirably, the wires are securably joined by welding the wired and further wherein the securably joined regions are welds.

The stent of this aspect of the present invention desirably may also have wires that terminate at the second open end, and adjacently juxtaposed wires are securably joined at the second open end to provide first securably joined regions, wherein at least one of the adjacently juxtaposed stent wires are extended past the first securably joined regions and looped such that the extended end abuts a proximal pair of stent wires; and further wherein the extended and looped wire is securably joined to the proximal pair of wires with second securably joined regions which are longitudinally offset from the first securably joined regions. Desirably, the wires are securably joined by welding the wired and further wherein the securably joined regions are welds. The first and the second welds may have a substantially same longitudinally extending extend. The first and the second welds may have longitudinally extending portions which overlap one and the other.

The stent of this aspect of the present invention may also be partially or fully coated with a polymeric material. The stent may further include hollow tubular graft disposed partially or fully over the interior or the exterior surface. Desirably, the graft is a polymeric material. The polymeric material may be selected from polyester, polypropylene, polyethylene, polyurethane, polynaphthalene, polytetrafluoroethylene, expanded polytetrafluoroethylene, silicone, and combinations thereof.

In another aspect of the present invention, a method for making an implantable stent is provided. The method includes the steps of (i) providing a plurality of elongate wires, wherein the elongate wires include composite wires to enhance visibility of the wires to provide improved external imaging of the wires in the body; and (ii) braiding the wires to form a hollow tubular structure having a tubular wall to define an interior surface and an exterior surface and having opposed open first and second ends, wherein the opposed open first and second ends are atraumatic ends. Desirably, the enhanced visibility is enhanced radiopacity and the external imaging is fluoroscopic or x-ray visualization.

The method this aspect of the present invention may further include the step of arranging the wires at the first end in a series of closed loops with each loop having an apex defined by a bend in one of the wires and having an opposed base defined by crossing of adjacent wires, wherein the apex of adjacent closed loops are longitudinally offset from one and the other.

The method this aspect of the present invention may also further include the steps of terminating the wires at the second end; aligning the wires at the second end into a plurality of mated adjacent wires to define a plurality of juxtaposed regions; and securably joining the mated adjacent wires to one and the other at the juxtaposed regions to define a closed loop at the second end. Desirably, the step of securably joining the wires includes welding the wires.

The method this aspect of the present invention may further include the steps of terminating the wires at the second end to form terminated wire ends; aligning the wires at the second end into a plurality of mated adjacent wires to define a plurality of juxtaposed regions; securably joining the mated adjacent wires to one and the other at the juxtaposed regions to define a plurality of securably joined regions; and smoothing the terminated wire ends by removing sharp edges from the wire ends. Desirably, the step of securably joining the wires includes welding the wires, and further wherein the securably joined regions are welds.

The method this aspect of the present invention may further include the steps of terminating the wires at the second end; aligning the wires at the second end into a plurality of mated adjacent wires to define a plurality of juxtaposed regions; extending at least one of the mated stent wires to provide an extended stent wire; looping the extended stent wire so the extended end abuts a proximal pair of stent wires; securably joining the mated adjacent wires to one and the other at the juxtaposed regions; and securably joining the extended and looped wire to the proximal pair of wires with a pair of longitudinally offset securably joined regions. Desirably, the step of securably joining the wires includes welding the wires, and further wherein the securably joined regions are welds.

In another aspect of the present invention, a stent delivery and deployment system is provided. The system includes a delivery catheter having a distal end; an elongate radially self-expanding stent having a distal end adjacent the distal end of the catheter; an elongate sheath retractably positioned about the stent so as to maintain the stent in a radially compressed delivery condition about the distal end of the catheter; and a retaining band positioned adjacent the distal end of the stent, the retaining band being retractable with the sheath so as to allow longitudinally progressive and radial expansion of the stent upon the retraction of the sheath for deploying the stent. The retaining band may include a radiopaque marker. The band may also be formed of a radiopaque material.

In yet another aspect of the present invention, a method of delivering and deploying an expandable stent includes the steps of disposing a radially expanding stent at a distal end of a delivery catheter; positioning a retractable sheath having a retaining band adjacent a distal end of the stent over the stent so as to maintain the stent in a radially compressed delivery condition; and retracting the sheath and the retaining band with respect to the distal end of the catheter to allow longitudinal progressive expansion of the stent. The sheath and the band are retracted together. The retaining band may include a radiopaque marker or is formed of a radiopaque material. The positioning step may further include the step of positioning the band at the distal end of the stent. Desirably, the stent is a braided stent having opposed first and second atraumatic open ends.

The stents, systems and methods of the present invention may be used at strictures or damaged vessel sites. Such sites may suitably include bodily tissue, bodily organs, vascular lumens, non-vascular lumens and combinations thereof, such as, but not limited to, in the coronary or peripheral vasculature, esophagus, trachea, bronchi, colon, biliary tract, urinary tract, prostate, brain, stomach and the like

BRIEF DESCRIPTION OF THE DRAWINGS

FIG. 14 depicts a stent having a covering of silicone according to the present invention.

FIG. 15 is a cross-sectional view of the stent of FIG. 14 showing an outer covering of silicone about the stent.

FIG. 16 is a cross-sectional view of the stent of FIG. 14 showing an inner covering of silicone about the stent.

DETAILED DESCRIPTION OF THE PREFERRED EMBODIMENT

Figure 1:
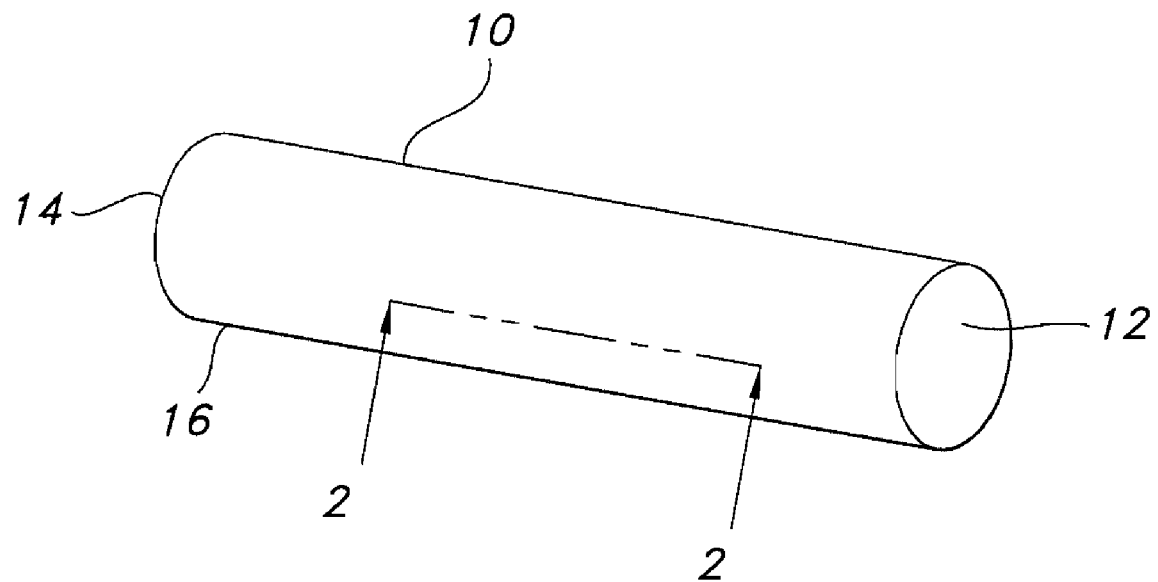
FIG. 1 is a perspective view of a hollow, tubular stent according to the present invention.
Figure 2:
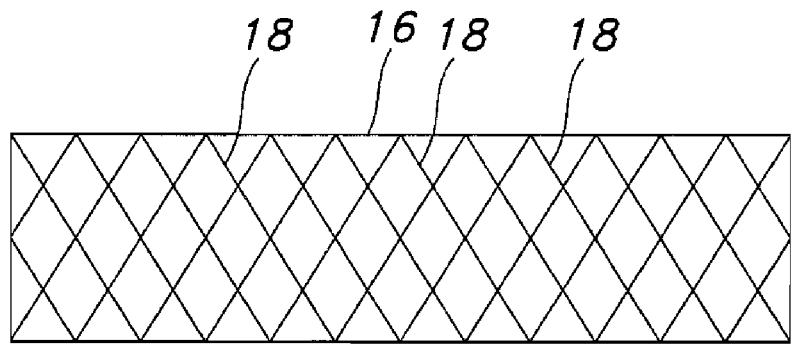
FIG. 2 is an expanded view of a wall portion of the stent of FIG. 1 taken along the 2-2 axis showing a plurality of stent wires.

FIG. 1 depicts stent 10 of the present invention. Stent 10 is a hollow tubular structure having opposed open ends 12, 14 and having a tubular wall 16 therebetween. A portion of the tubular wall 16 is depicted in FIG. 2 as having a plurality of elongate wires 18 formed into the tubular wall 16. The elongate wires 18 traverse the length of the stent 10 in a direction traverse to the longitudinal length of the stent 10. The elongate wires 18 may be formed into the tubular wall 16 by braiding the wires 18, winding the wires 18, knitting the wires 18, and combinations thereof. Preferably, the wires 18 are braided to form the tubular wall 16.

As used herein the term braiding and its variants refer to the diagonal intersection of elongate filaments, such as elongate wires, so that each filament passes alternately over and under one or more of the other filaments, which is commonly referred to as an intersection repeat pattern. Useful braiding patterns include, but are not limited to, a diamond braid having a 1/1 intersection repeat pattern, a regular braid having a 2/2 intersection repeat pattern or a hercules braid having a 3/3 intersection repeat pattern. The passing of the filaments under and over one and the other results in slidable filament crossings that are not interlooped or otherwise mechanically engaged or constrained.

Figure 3:
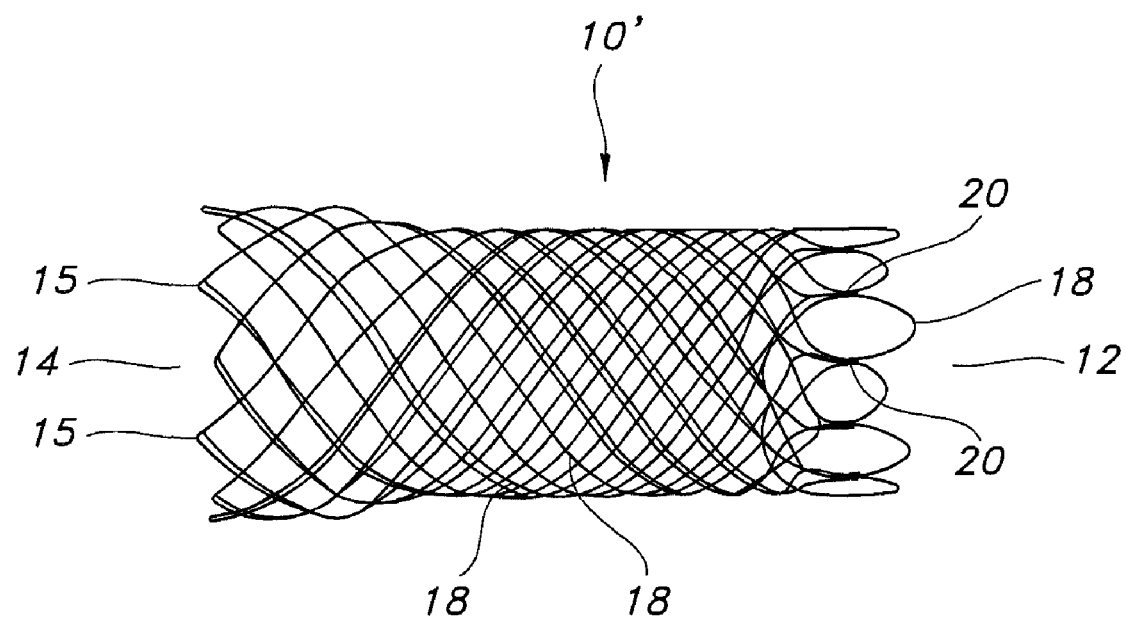
FIG. 3 depicts a braided stent with a closed-end loop design having a plurality of welds at the closed end according to the present invention.

A joined or welded stent 10' according to the present invention is depicted in FIG. 3. The elongate wires 18 terminating at open end 12 are mated and adjacently mated wires are secured to one and the other by welds 20 or by other suitable means. For example, the wires 18 may be welded together through use of a welding material or the wires 18 may be heatingly and/or meltably fused together without the use of a welding material. Further, the wires 18 may mechanically joined, such as, but not limited to, through the use of small-sized or micro-fabricated clamp, crimpable tube, hypotube, and the like. The joining of three adjacently mated wires 18 and the welding thereat is depicted in further detailed in FIGS. 4-6. The positioning of adjacently mated wires to form closed-loop end designs is further described in U.S. Application No. 60/472,929, filed May 23, 2003, which was filed May 24, 2004 as U.S. application Ser. No. 10/852,495 and published as U.S. Patent Application Publication No. 2005/0049682 A1, the contents of all of which are incorporated herein by reference. The stent 10' depicted in FIG. 3 includes 24 wires or filaments 18 of biocompatible material. The wires are relatively thin at a diameter of about 0.01 inches. The number of wires and the diameters of the wires, which may be the same or different, depicted in FIG. 3 are not limiting, and other numbers of wires and other wire diameters may suitably be used. Desirably, an even number of wires are used, for example from about 10 to about 36 wires.

The stent 10' depicted in FIG. 3 has atraumatic open ends 12, 14. As used herein, the phrase "atraumatic end" and it variants refer to a terminal end of a stent which is free of sharp wire ends or other sharp projections or deformities which may cause trauma when implanted into a bodily lumen. For example, as described in further detail below, open end 14 of the stent 10' is atraumatic because the stent 10' is braided such that no ends of the wires 18 end at this end of the stent 10'. In other words, stent 10' may be braided such that all the ends of the wires 18 are distal from the end 14, for example, by commencing the braiding of the stent 10' with wires 18 that are bent in a smooth configuration so that the loop ends 15 of the end 14 have no sharp or traumatically pointed bends or projections. Moreover, as described in further detail below, the end 12 of the stent 10' is atruamatic because, among other things, even though the wires 18 terminate proximal to the end 14 of the stent 10', certain wires 18 are extended and looped back to provide an atruamatic end with, for example, no sharp or traumatically pointed bends, no sharp wire ends, no other traumatically sharp projections or deformities and the like.

Figure 4:
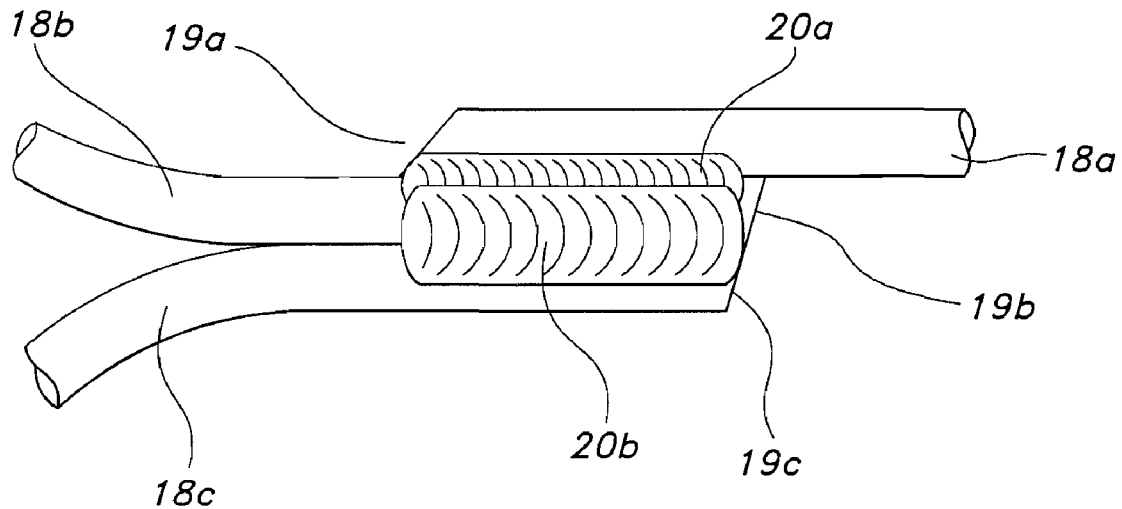
FIGS. 4 and 5 are expanded views of weld areas of FIG. 3 illustrating smooth terminated wire ends.
Figure 5:
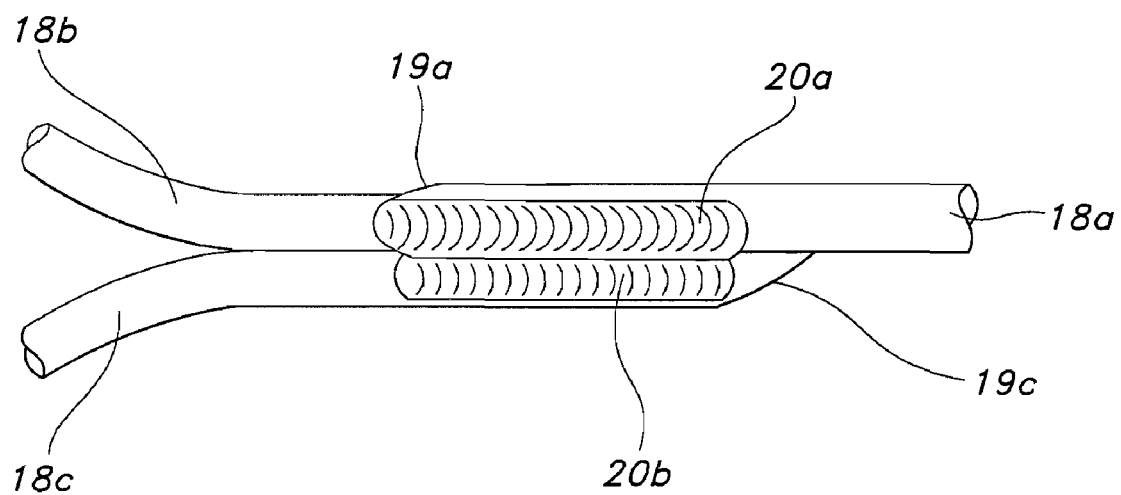
Figure 6:
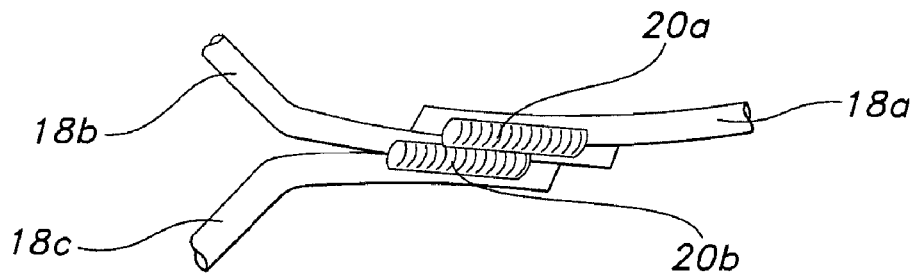
FIG. 6 is an expanded view of the weld of FIG. 3 showing a pair of offset welds joining three adjacently juxtaposed stent wires.

Adjacently welded wires according to the present invention are depicted further detail in FIGS. 4-6. The terminated wire ends 19*a*, 19*b* and 19*c* are smoothed to remove sharp edges from the ends. As depicted in FIG. 4, terminal wire ends 19*b* and 19*c* are diagonally cut to remove shape edges as compared to wires that are not diagonally cut (not shown). Further, as depicted in FIG. 5, terminal wire end 19*a* is smoothed to a have a curved portion or a portion having a radius of curvature. Such smoothing may be achieved by use of a laser beam over the terminal end 19*a*. Heat generated by the laser beam melts the wire material forming a smooth, curved shape. Surface tension of the molten wire material allows the material to flow out evenly. These techniques for smoothing the terminal wire ends may be used individually or in combination. In other words, terminal ends 19*a*, 19*b* and 19*c* may be, individually or in combination, diagonally cut and/or partially melted to provide a smooth terminal wire end.

Additionally, the terminal wire ends 19*a*, 19*b* and 19*c* may be chemically or electro-chemically treated to remove sharp ends. Details of chemically or electro-chemically removing processes are described in U.S. patent application Ser. No. 10/845,844, filed May 14, 2004, the contents of which are incorporated herein by reference.

Further, as depicted in FIGS. 4-5, a securably joined region or weld 20*a* joins wires 18*a* and 18*b*, and a securably joined region or weld 20*b* joins wires 18*b* and 18*c*. Securably joined regions or welds 20*a* and 20*b* are depicted as substantially overlapping one and the other. The present invention, however, is not so limited. As depicted in FIG. 6, a securably joined region or weld 20*a* is longitudinally offset from a securably joined region or weld 20*b*. Desirably, the length of the securably joined regions or welds 20*a* and 20*b* are substantially similar. Also desirably, a portion of a securably joined region or weld 20*a* overlaps a portion of a securably joined region or weld 20*b*. Such offsetting and/or overlapping of the securably joined regions or welds provide greater fatigue life. For example, the offset and overlapping welds 20*a* and 20*b* of FIG. 6 surpassed 500,000 cycles of stent contraction and/or expansion without fatigue failure. Similar welds that are not offset and overlapping do not pass such fatigue testing.

Useful welding methods include, but are not limited to, laser welding, electron beam welding, resistance welding, tungsten inert gas welding, metal inert gas welding and combinations thereof. In laser and electron beam welding the wires are partially melted by the energy provided by the laser or electron beam. In gas tungsten arc welding (GTAW or TIG welding), an arc is formed between an electrode, typically tungsten, and the metal being welded. In metal inert gas (MIG) welding, an arc is generated between a filler electrode and the metal being welded with metal melted from the filler electrode being added to the metal being welded. Resistance welding uses the application of electric current and sometimes mechanical pressure to create a weld between two pieces of metal. The weld areas may be shielded with an inert gas. Suitable, but non-limiting, inert gasses include argon and argon/gas admixtures, such as argon/hydrogen or argon/helium.

The wires or filaments 18 are made from a biocompatible material or biocompatible materials. Useful biocompatible materials include biocompatible metals, biocompatible alloys and biocompatible polymeric materials, including synthetic biocompatible polymeric materials and bioabsorbable or biodegradable polymeric materials. Desirably, the wires 18 are biocompatible metals or alloys made from, but not limited to, nitinol, stainless steel, cobalt-based alloy such as Elgiloy, platinum, gold, titanium, tantalum, niobium, polymeric materials and combinations thereof. Useful synthetic biocompatible polymeric materials include, but are not limited to, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, silks and polytetrafluoroethylenes. The polymeric materials may further include a metallic, a glass, ceramic or carbon constituent or fiber. Useful and nonlimiting examples of bioabsorbable or biodegradable polymeric materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly(phosphate ester) and the like. Wires made from polymeric materials may also include radiopaque materials, such as metallic-based powders or ceramic-based powders, particulates or pastes which may be incorporated into the polymeric material. For example, the radiopaque material may be blended with the polymer composition from which the polymeric wire is formed, and subsequently fashioned into the stent as described herein. Alternatively, the radiopaque material may be applied to the surface of the metal or polymer stent. In either embodiment, various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent may be selectively made radiopaque at desired areas along the wire or made be fully radiopaque, depending on the desired end-product and application. Further, the wires 18 have an inner core of tantalum, gold, platinum, iridium or combination of thereof and an outer member or layer of nitinol to provide a composite wire for improved radiocapicity or visibility. Desirably, the inner core is platinum and the outer layer is nitinol. More desirably, the inner core of platinum represents about at least 10% of the wire based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Patent Application Publication 2002/0035396 A1, the contents of which is incorporated herein by reference. Preferably, the wires 18 are made from nitinol, or a composite wire having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof, preferably nitinol. The material of the cathode is no critical and can be made out of any suitable metal. The filling weld material, when present, and the wire 18 may be made of the same material, for example nitinol. The filling weld material, when present, may also be fully or partially radiopaque through use of the below-described materials.

As depicted in FIG. 3, stent 10' is a braided stent having atraumatic ends 12, 14. The stent includes filaments or wires 18 that are fully or partially composite filaments or wires 18 to enhance visibility of the wires to provide improved external imaging of the wires in the body. Desirably, the enhanced visibility is enhanced radiopacity to provide improved fluoroscopic or x-ray visualization of said wires in the body. Enhanced radiopacity may be achieved by using the above-described radiopaque materials in combination with a biocompatible stent material. Such radiopaque materials are believed to be more visible under fluoroscopic or x-ray visualization due to their higher density than the corresponding biocompatible stent material. The present invention, however, is not limited to a stent with improved fluoroscopic or x-ray visualization. For example, the stent 10' may also have improved external imaging under magnetic resonance imaging (MRI) and/or ultrasonic visualization techniques. Magnetic resonance imaging is produced by complex interactions of magnetic and radio frequency fields. Materials for enhancing MRI visibility include, but not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the stent 10' of the present invention may include ultrasound resonant material, such as but not limited to gold.

The stent wires 18 at the open end 14 are bent to form closed loop ends 15 thereat. As depicted in FIG. 3, the loop ends 15 are substantially angular having approximately or about a 90° bend. The radius of curvature at the point of the bend is desirably minimized. In other words, the loop end 15 desirably has an angularly bent portion between substantially straight wire portions that do not otherwise have a portion with a significant radius of curvature. The loop ends 15, however, are not limited to angular bends of 90° and other bend angles may suitably be used. For example, angular bends with a bend angle from about 30° to about 150° are also useful. Other useful bend angles include from about 60° to about 120°, from about 70° to about 110°, from about 80° to about 100°, from about 85° to about 95°, and the like.

The loop ends 15, however, are not limited to substantially angular bend-containing loops and other shaped loop ends, such as semi-circular, semi-elliptical and other smoothly curved or substantially smoothly curved loops, including but not limited to cathedral-shaped loops, may suitably be used.

Thus, in one desirable aspect of the present invention, a stent is provided with opposed atraumatic, closed-looped ends. One of the atraumatic ends may include closed loops having substantially angular bends, as described above, and the other opposed atraumatic end may include a cathedral type arch or loop, as described below.

As depicted in FIGS. 7-11, certain stent wires 56, 62 may be extended beyond adjacent wires 50, 64, and then looped back to proximal wires 52, 60 and 58, 64, respectively. Adjacent portions of wires 50 and 56 are abuttingly disposed at juxtaposed region 68. Similarly, adjacent portions of wires 52 and 60 and the adjacent portion of the extended loop portion 66 are juxtaposingly disposed at abutting region 70; adjacent portions of wires 54 and 62 are juxtaposingly disposed at juxtaposed region 72; and adjacent portions of wires 58 and 64 and the adjacent portion of the extended loop portion 67 are juxtaposingly disposed at juxtaposed region 74. Desirably, the juxtaposingly disposed wire portions in the juxtaposed regions are substantially parallel to one and the other, for example, but not limited to, being within about plus or minus 10 degrees of parallelism to one and the other, preferably, but not limited to within about plus or minus 5 degrees of parallelism. As used herein the term "juxtaposed" and its variants refer to wires that are proximal to one and the other, desirably in touching relationship. The wires may be in a side-to-side relationship, an end-to-end relationship, a crossing over relationship, a butting relationship, and the like.

Figure 7:
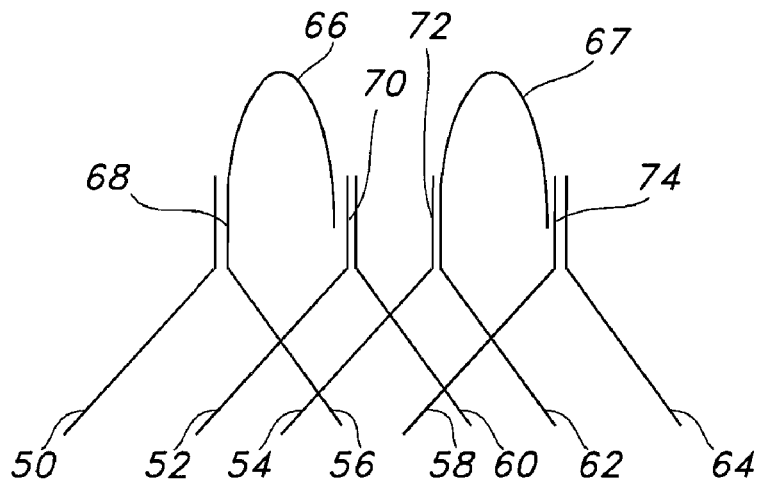
FIGS. 7-11 depict an arch with equilateral sides and an apex in a closed-end loop design according to the present invention.
Figure 8:
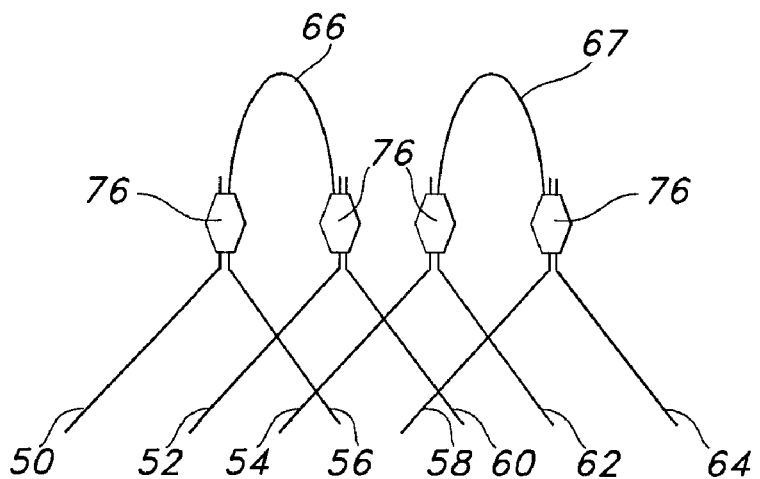
Figure 33:
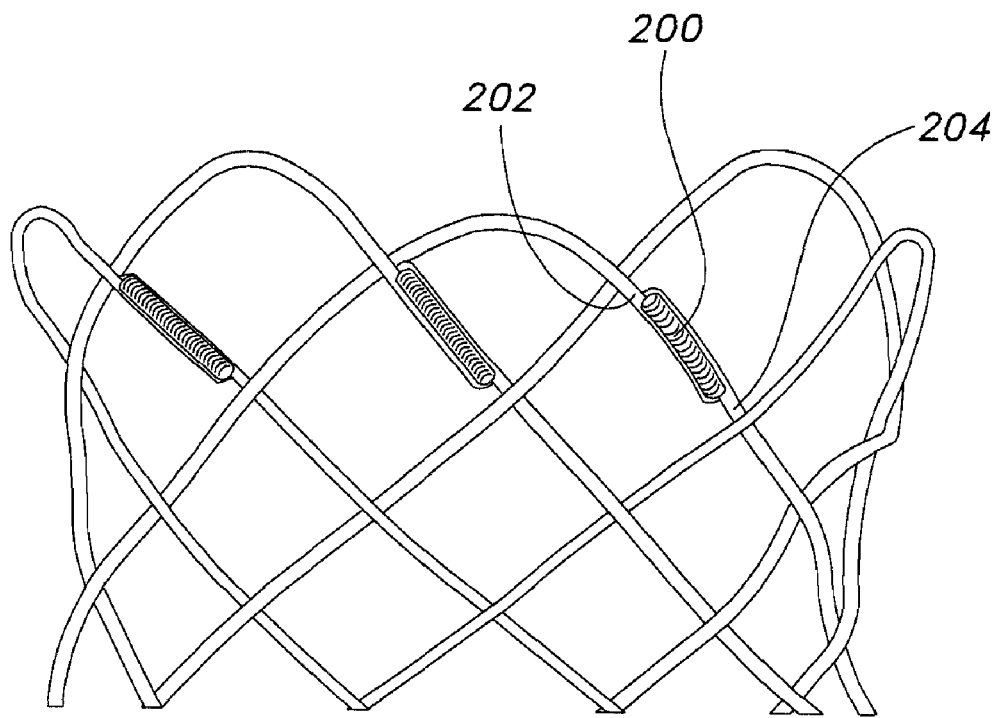
FIG. 33 depicts the welding of looped and braided wires within the braid structure of the stent of the present invention.

As depicted in FIG. 7, the wires at the juxtaposed regions 68, 70, 72, 74 may be secured by welds 76. Desirably, welds 76 are offset and overlapping pair of welds as described above. The present invention, however, is not limited to the welding of the longitudinally disposed wire portions as depicted in FIGS. 7-8. For example, as depicted in FIG. 33, a weld joint 200 may securably join juxtaposed wires 202 and 204 which form an in integral part of the braid. Desirably, the weld joint 200 is positioned inside the adjacent loop, i.e., after adjacent wires cross, to provide higher radial strength and to withstand higher radial compression forces.

Figure 9:
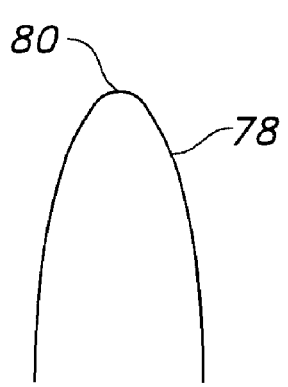

Desirably, the extended loop portions 66, 67 are of an arch with equilateral sides' design, which can be referred to as a cathedral type of arch or loop. As depicted in FIG. 9, the equilaterally arched loop 78 has an apex or vertex 80. As used herein, the term "vertex" and its variants refer to the intersection of two geometric lines or curves. As used herein, the term "apex" and its variants refer to a vertex at the top or summit of a loop. Desirably, the equilaterally arched loop 78 does not have any bends, which are defined as areas having dissimilar curvatures on either side of a point, except for the apex 80. In other words, the equilaterally arched loop 78 has an apex, but not other sharp bends. Desirably, the equilaterally arched loop 78 has one vertex (or apex 80) having similar curvatures on either side of the one vertex (or apex 80), but does not contain a second vertex having dissimilar curvatures on either side of the second vertex.

The equilaterally arched loop design offers several advantages, including reduced deployment force, as compared to loop designs having a plurality of vertices or sharp bends. When a stent is constrained on or in a delivery system (not shown), the multiple sharp bends in the end loops of the stent typically impinge on the wall of the delivery system and become slightly imbedded thereat, thereby distorting the outer sheath of the delivery system. This results in significantly greater deployment force values. Further, as the equilaterally arched loop has only one sharp bend, i.e., its apex, and is defined otherwise by a gradual curvature, the gradual curvature portions do not become imbedded in the wall of the delivery system, thereby significantly reducing the resultant deployment force.

Figure 10:
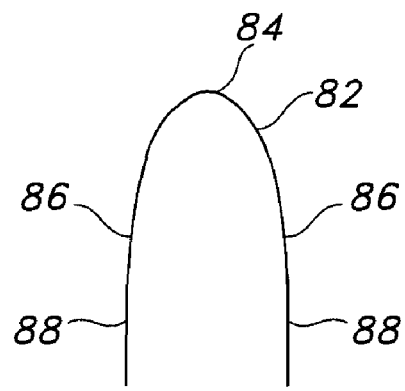
Figure 11:
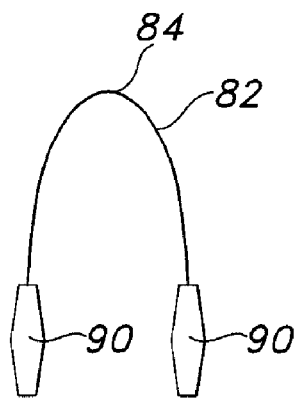
Figure 13:
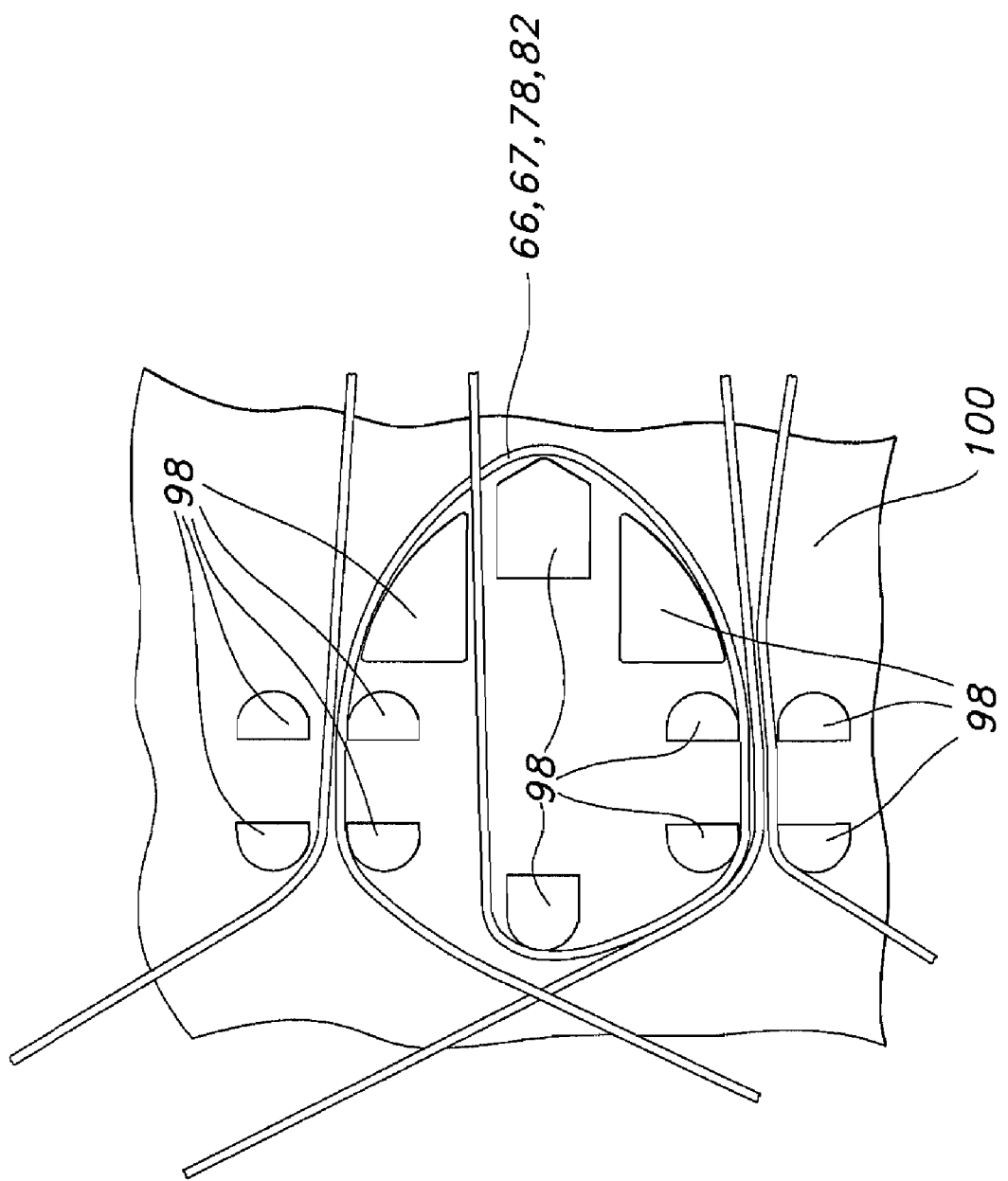
FIG. 13 depicts a mandrel having shaped pins for forming the closed loops of FIGS. 7-11.

In another aspect of the present invention as depicted in FIGS. 10 and 11, an equilaterally arched loop 82 may have an apex 84 and vertices 86 having substantially straight line portions 88. In such a case, the vertices 86 and the straight line portions 88 have low profile welds 90 there over to adjoin other adjacently abutting stent wires (not shown). The equilaterally arched loops 66, 67, 78, 82 of the present invention may be suitably formed by winding their stent wires about shaped pins 98 on a mandrel 100 as depicted in FIG. 13. Further details of the cathedral type of arch or closed-loop configuration may be found in U.S. application Ser. No. 10/845,844, filed May 15, 2004, the contents of which are incorporated herein by reference.

Figure 32:
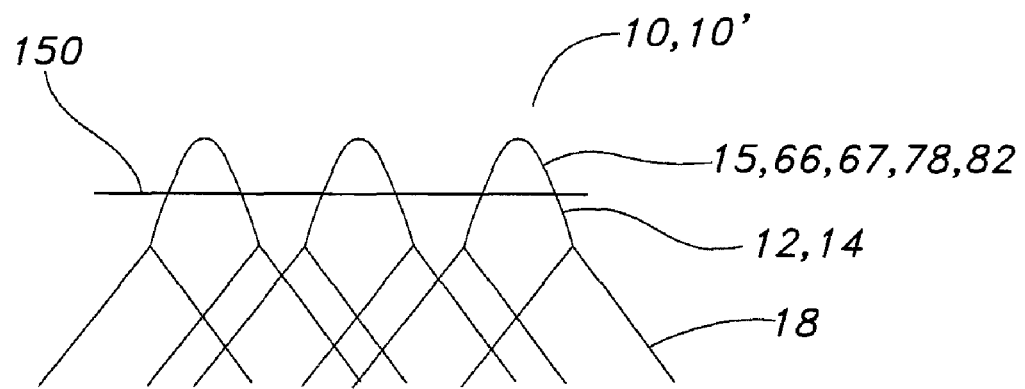
FIG. 32 depicts a suture loop attached to a portion of the stent of the present invention.

Further, either or both of the ends 12, 14 of the stent 10, 10', including end 12 with equilaterally arched loops 66, 67, 78, 82, may have a suture or sutures attached thereto. Such sutures, which may be textile, polymeric or metallic, are useful for positioning, repositioning, and/or removing the stent 10, 10'. Useful polymeric materials include polyester, such as braided polytetrafluoroethylene-impregnated polyesters. As depicted in FIG. 32, a suture loop 150 may be disposed at the either or both ends 12, 14 of the stent 10, 10'. Desirably, the suture loop 150 is disposed at the end 12. As depicted in FIG. 32, the suture loop 150 is looped among the loop portions, such as portions 66, 67, 78 or 82, of the stent 10, 10'. The suture loop 150 may be used by a practitioner for re-positioning and/or removing the stent 10, 10'. The suture loop 150 may be grabbed by suitable forceps, such as rat-tooth forceps (not shown). Upon grabbing the suture loop 150 and applying a pulling force thereto, the suture loop 150 cinches and contracts the end 12 or 14 of the stent 10, 10', thereby easing movement of the stent 10, 10' in vivo. The suture loop may be relatively taut over the stent end of may be loosely disposed thereat so as to have some slack. The suture loop 150 is a closed-loop device where the ends of the thread or strand forming the suture loop are securably joined together by, for example, tying, gluing and/or fusing the end together. Ultrasonic fusing of polymeric suture thread, in particular knots formed in the thread, is also useful with the present invention. Further details of suitable fused suture knots may be found in U.S. patent application Ser. No. 11/073,779, filed Mar. 7, 2005, the contents of which are incorporated herein by reference. The present invention is not so limited and other designs useful for positioning, repositioning, and/or removing stent 10 may suitably be used. Further details of such other positioning and/or repositioning designs may be found in U.S. application Ser. No. 10/845, 844, filed May 15, 2004, which published as U.S. Patent Application Publication No. 2005/0209639 A1, the contents of all of which are incorporated herein by reference. Further, a retrieval and/or repositioning loop may be integrally formed into the braided stent structure. Such an integral retrieval and/or repositioning loop includes at least of two wires formed into the repositioning and/or retrieval loop which has an elongated portion circumferentially disposed at the end of the stent. The reposition and/or retrieval loop includes two sections which run adjacent to each other prior to crossing to permit grabbing of both sections simultaneously by a practitioner. Further details of such a reposition and/or retrieval loop may be found in U.S. Provisional Application No. 60/680,689, titled "Integrated Stent Repositioning and Retrieval Loop", filed May 13, 2005, the contents of which are incorporated herein by reference.

Moreover, the repositioning and/or retrieval of the stent 10, 10' may also be accomplished without the use of the above-described suture loop 150 and/or the integral loop. For example, a repositioning and/or retrieval device (not shown), such as a catheter, endoscope or the like, may incorporate grabbing detents which may directly engage the loops 66, 67, 78, 82 of the stent 10, 10'. Such a repositioning and/or retrieval device may also be able to radially compress the stent 10, 10' at the loop ends 66, 67, 78, 82 to facilitate repositioning and/or retrieval of a deployed stent, for example by withdrawing the stent 10, 10' into a lumen of the repositioning and/or retrieval device. A stent restraining device, such as a polymeric sleeve, may be positioned within the lumen of the repositioning and/or retrieval device to secure the stent therein during repositioning and/or retrieval. Further, the lumen need not be a substantially cylindrical lumen, and it may have a conical portion, for example in the shape of a funnel, which may be useful for transitioning the stent 10, 10' from it deployed diameter to a smaller diameter for securement within the lumen of the repositioning and/or retrieval device.

In one embodiment of the present invention, one end of the stent may have weld joints which, due to their positioning, provide higher radial strength, i.e., the resultant stents can withstand higher radial compressive forces without fear of weld failure. In these embodiments, the weld joint 20a, 20b may be positioned between the crossings of adjacent wires 18a, 18b, 18c, as shown in FIGS. 4-6.

In another aspect of the present invention, the loop ends at the open end 14 of the stent 10 may be longitudinally staggered or offset from one and the other. Desirably, each loop 15 is staggered in alternative long and short longitudinally extending loops. Such a staggering or offsetting of the loop ends 15 reduces deployment forces for delivery of the stent. By longitudinally staggering or offsetting the length and the alignment of the loop ends 15, the force required to deliver the stent 10 to an intended bodily site is reduced as compared to a stent not having a staggered loop end.

When a stent is tightly constrained in a delivery system, each loop extends to exert a force on a wall of the delivery system, possibly embedding itself into the wall to some extent. When the loops are longitudinally staggered, the force exerted by each loop is laterally distributed in a more even fashion. Such staggering reduces the force required to move the stent from the wall of the delivery system, thereby reducing the overall deployment force. In addition, staggered loops are less likely to interfere with each other as compared to non-staggered loops, again reducing the deployment force. In other words, staggered loops will less likely impede the delivery of the stent as compared to non-staggered loops.

Figure 12:
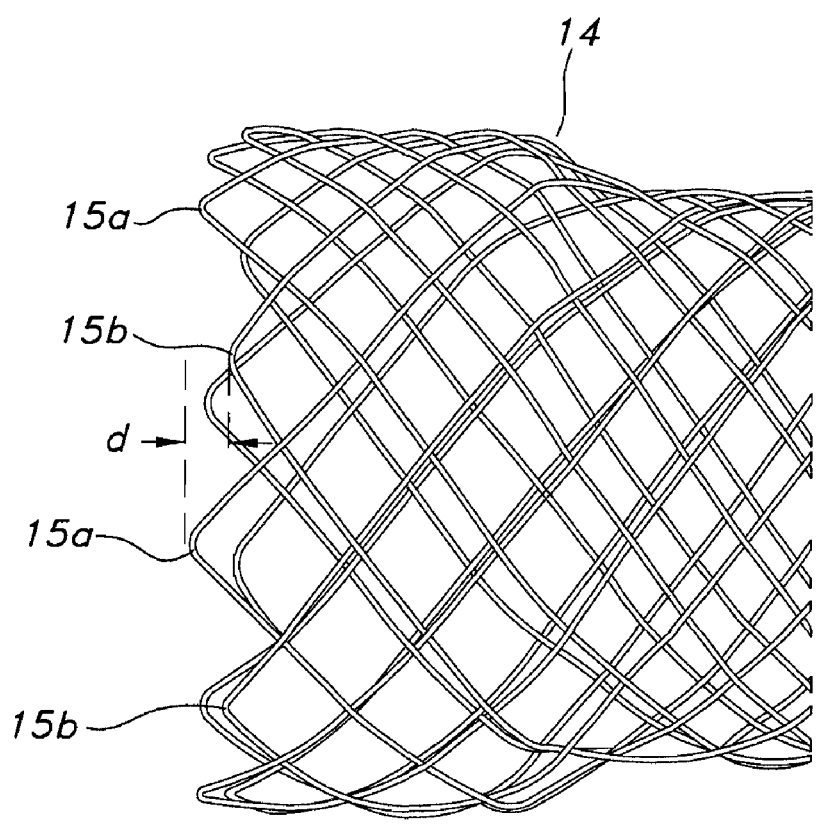
FIG. 12 depicts an exploded, partial view of the left-side stent end of FIG. 3.

As depicted in FIG. 12, which is a partial exploded view of a portion of the stent end 14 of FIG. 3, stent loops 15a are staggered from stent loops 15b. The staggering of the loops results in a longitudinal offset, d, between the apexes or apices of the adjacent loops. As depicted in FIG. 12, one set of loops 15a are offset from another set of loops 15b by a single longitudinal offset, d. The present invention, however, is not so limited. For example, the stent end 14 may have staggered loop ends having more than one or a plurality of longitudinal offsets. The staggered loop ends 15a, 15b with either a single offset or a plurality of offsets may suitably be formed by providing a mandrel with longitudinally offset pins (not shown) and commencing braiding or otherwise positioning the stent wires thereat.

As depicted in FIG. 14, the stent 10 may be fully, substantially or partially covered with a polymeric material 102. The covering may be in the form of a tubular structure. One nonlimiting example of a polymeric material is silicone. The polymeric material and/or silicone 102 may be disposed on external surfaces 104 of the stent 10, as depicted in FIG. 15, or disposed on the internal surfaces 106 of the stent 10, as depicted in FIG. 16, or combinations thereof. The silicone covering may be suitably formed by dip coating the stent. Details of such dip coating may be found in U.S. Pat. No. 5,875,448, the content of which is incorporated herein by reference. The present invention is not limited to forming the silicone film by dip coating, and other techniques, such as spraying, may suitably be used. After applying the silicone coating or film to the stent, the silicone may be cured. Desirably, the curing is low temperature curing, for example from about room temperature to about 90° C. for a short period of time, for example from about 10 minutes or more to about 16 hours. The cured silicone covering may also be sterilized by electronic beam radiation, gamma radiation ethylene oxide treatment and the like. Further details of the curing and/or sterilization techniques may be found in U.S. Pat. No. 6,099,562, the content of which is incorporated herein by reference. Argon plasma treatment of the cured silicone may also be used. Argon plasma treatment of the cured silicone modifies the surface to the cured silicone to, among other things, make the surface less sticky.

With any embodiment of the stent 10, 10', 128 is usable to maintain patency of a bodily vessel, such as in the coronary or peripheral vasculature, esophagus, trachea, bronchi colon, biliary tract, urinary tract, prostate, brain, and the like. Also, the stent 10, 10' may be treated with any of the following: anti-thrombogenic agents (such as heparin, heparin derivatives, urokinase, and PPack (dextrophenylalanine proline arginine chloromethylketone); anti-proliferative agents (such as enoxaparin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

Further, with any embodiment of the stent 10, 10' the general tubular shape may be varied. For example, the tubular shape may have a varied diameter, an inwardly flared end, an outwardly flared end and the like. Further, the ends of the stent may have a larger diameter than the middle regions of the stent. A braided stent with outwardly flared ends is further described in U.S. Pat. No. 5,876,448, the contents of which are incorporated herein by reference.

Figure 17:
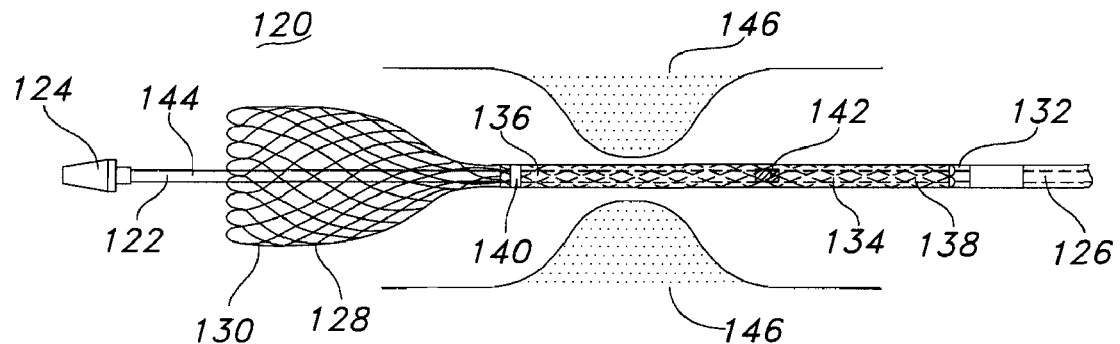
FIGS. 17-22 depict a stent deployment and delivery system of the present invention.
Figure 18:
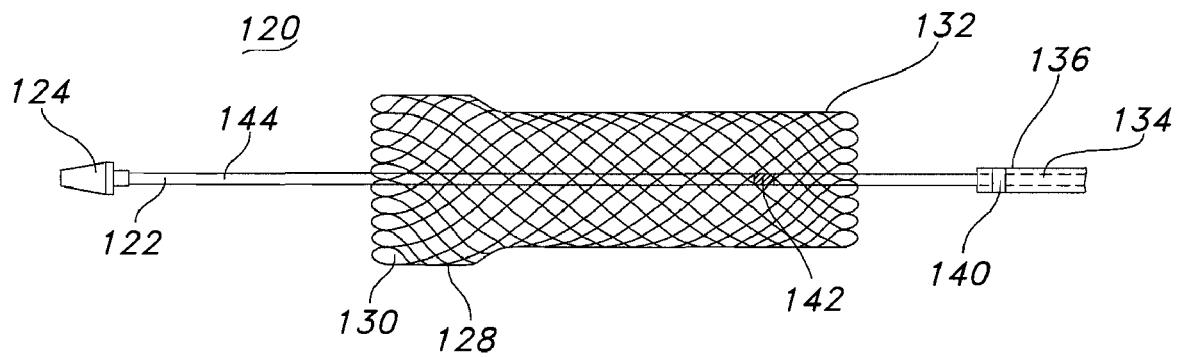
Figure 19:
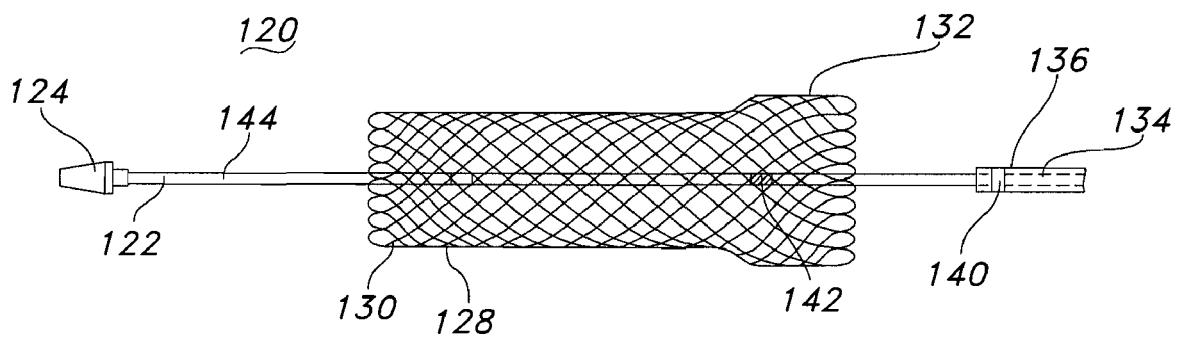
Figure 20:
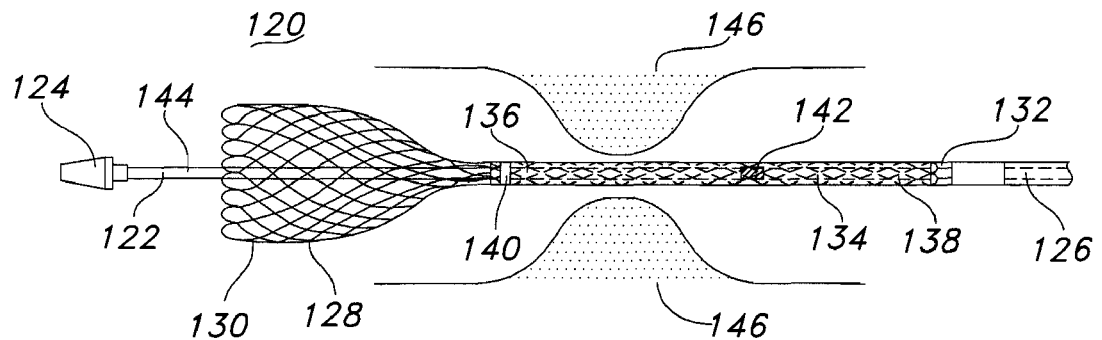

In another aspect of the present invention, a stent delivery and deployment system is provided. As depicted in FIGS. 17-22, a stent delivery and deployment system 120 is provided. The system 120 includes a catheter 122 having a distal end 124 and a proximal end 126; a stent 128 having a distal end 130 and a proximal end 132; a retractable sheath 134 having a distal end 136 and a proximal end 138; a marker band 140 disposed at the distal end 136 of the delivery sheath 134; and a post-deployment marker band 142 disposed on an inner member 144 of the catheter 122 toward the proximal end 126 of the catheter 122; interrelated as shown. The marker band 140 may be placed at the distal end 136 of the sheath 134. FIGS. 17 and 20 depict a partially deployed stent 128. Prior deployment sheath 134 substantially covers or even extends beyond the distal end 130 of the stent 128. The marker band 140 is disposed to overlap the distal end 130 of the stent 128 in the pre-deployment stage. Typical prior art systems have a marker band positioned on the sheath, but beyond the stent, which complicates stent placement. Another reason for such marker placement 140 overlapping the stent 128 is for constraining the stent 128 prior to deployment. Without the marker band 140 placed at the distal location of the stent, the stent may expand into the polymeric sheath during sterilization and/or storage. Such expansion induces higher frictional forces at this location, ultimately increasing the deployment force required to deploy the stent. When a marker band does not overlap the stent, deployment forces in the range of about 14 pounds-force is required. The system 120 of the present invention requires significantly less deployment force, approximately in the range of about 5 to about 6 pounds-force. Desirably, deployment forces with the system 120 of the present invention are less than about 10 pounds-force, more desirably less than about 8 pounds-force, preferably less than about 7 pounds-force or less.

The system 120 of the present invention a post-deployment marker band 142 disposed on an inner member 144 of the catheter 122 toward the proximal end 126 of the catheter 122. For delivery of the stent 128, the post-deployment marker band 142 is placed proximally or before the stricture or damaged vessel site 146. Such placement ensures that the stent 128 will always completely span the vessel site 146 even when the stent 128 foreshortens as it expands during delivery. The stricture or damaged vessel site 146 may suitably include bodily tissue, bodily organs, vascular lumens, non-vascular lumens and combinations thereof, such as, but not limited to, in the coronary or peripheral vasculature, esophagus, trachea, bronchi, colon, biliary tract, urinary tract, prostate, brain, stomach and the like The markers 140 and 142 may comprise any useful radiopaque material or materials including any metal or plastics being radiopaque or capable of being impregnated with radiopaque materials. Useful radiopaque materials include, but are not limited to gold, barium sulfate, ferritic particles, platinum, platinum-tungsten, palladium, platinum-iridium, rhodium, tantalum or combinations thereof. The sheath 134 may comprise any plastic or polymeric material, desirably a somewhat hard but flexible plastic or polymeric material. The sheath 134 may be transparent or translucent, desirably substantially or partially transparent. Furthermore, the sheath 134 may be constructed of any suitable biocompatible materials, such as, but not limited to, polymers and polymeric materials, including fillers such as metals, carbon fibers, glass fibers or ceramics. Useful sheath materials include, but are not limited, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, styrene-butadiene copolymers, polyethers, such as fully or partially halogenated polyethers, and copolymers and combinations thereof.

Figure 21:
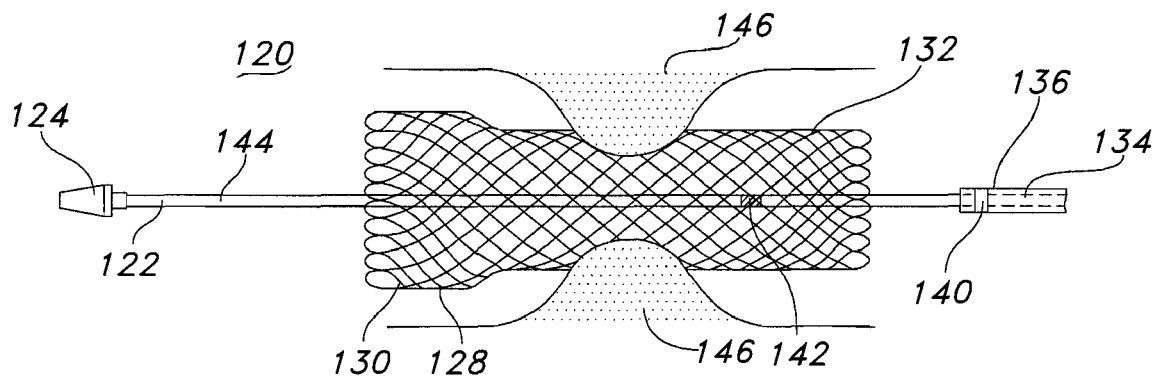
Figure 22:
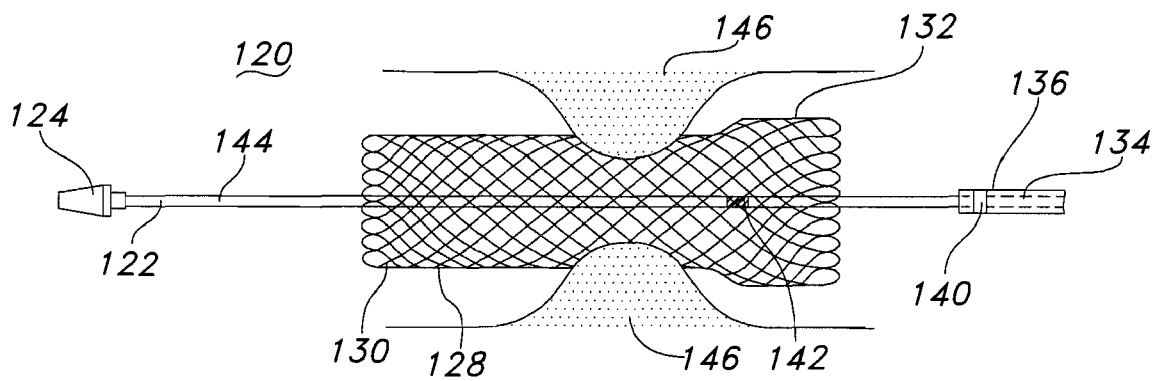

It may be noted that FIGS. 17 and 20 depict a partially deployed stent 128. FIGS. 18 and 21 depict a colonically deployed stent with the enlarged stent portion 130 being distal to the site 146. FIGS. 19 and 22 depict a duodenally deployed stent with the enlarged stent portion 132 being proximal to the site 146.

Figure 23:
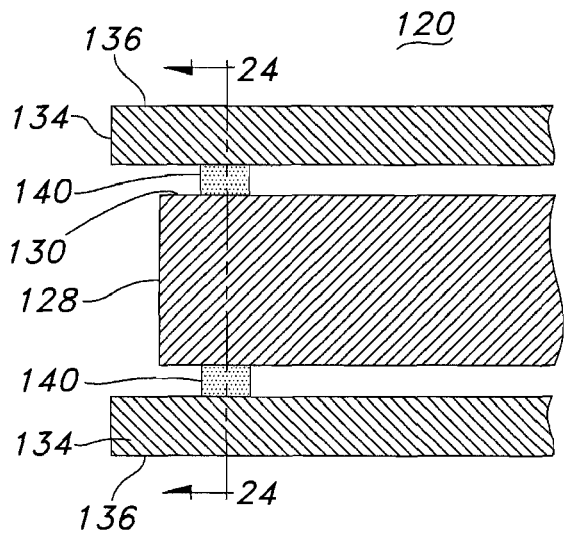
FIGS. 23-31 depict radiopaque marker placement details according to the stent deployment and delivery system of FIGS. 17-22.
Figure 24:
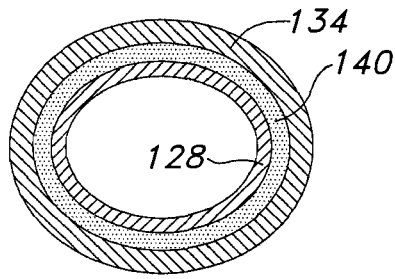

FIGS. 23-31 depict additional details of the arrangement of the marker 140 with the system 120 of the present invention. As depicted in FIG. 23, the marker 140 is disposed between the sheath 134 and the stent 128 at the distal end 136 of the sheath 134 with the marker 140 being placed proximal to the distal end 130 of the stent 128. Although the distal end 136 of the sheath 134 is depicted as covering and extending beyond the distal end 130 of the stent 128, the present invention is not so limited. The distal end 136 of the sheath 134 may be flush or substantially flush with the distal end 130 of the stent 128 (not shown). FIG. 24 is a cross-sectional view of the system 120 taken along the 23-23 axis. As depicted in FIG. 24 the sheath 134, the stent 128 and the marker 140 are continuous tubular or cylindrical members. The present invention, however, is not so limited. For example, the marker 140 need not be a continuous tubular member, but may be, for example, a segmented member.

Figure 25:
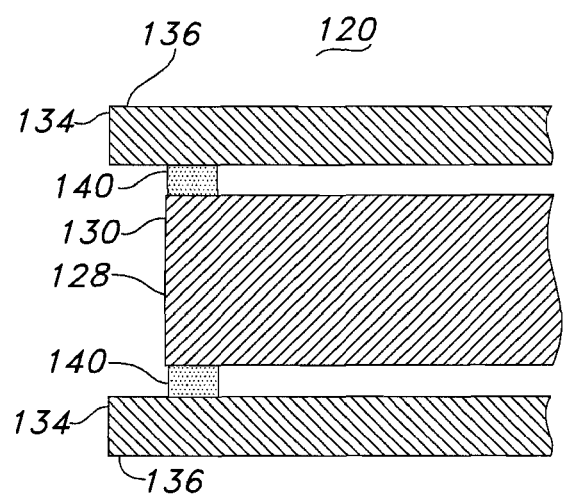
Figure 26:
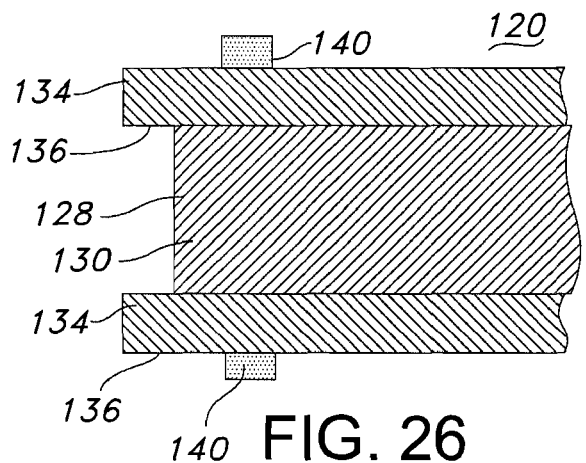
Figure 27:
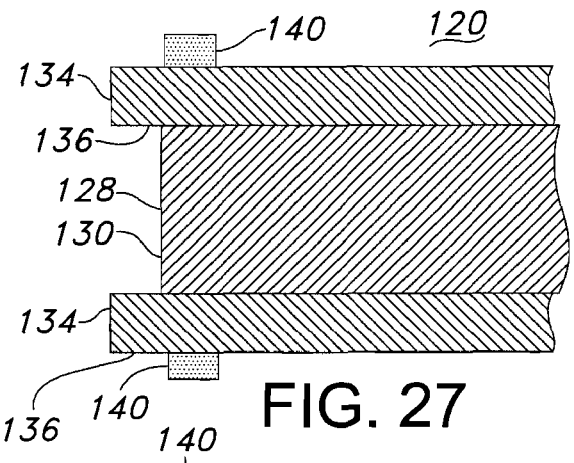

As depicted in FIG. 26, the marker 140 may be disposed over the outside surface or exterior portion of the sheath 134. As depicted in FIGS. 25 and 26 the marker 140 may be adjacently disposed, including substantially disposed, to or over the distal end 130 of the stent 128.

Figure 28:
Figure 29:
Figure 30:
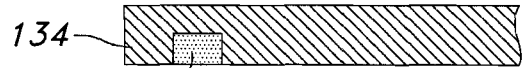
Figure 31:

FIGS. 28-31 depict alternate embodiments of the placement of the marker 140 with the sheath 134. As depicted in FIG. 28, the marker 140 may be fully embedded within the sheath 134. As depicted in FIG. 29, the marker 140 may interrupt or partially interrupt the sheath 134. As depicted in FIG. 30, the marker may be partially embedded within the sheath 134, but being exposed at the interior or luminal surface of the sheath 134, which is generally depicted as the bottom portion of the sheath 134 in FIG. 30. As depicted in FIG. 31, the marker may be partially embedded within the sheath 134, but being exposed at the exterior surface of the sheath 134, which is generally depicted as the upper portion of the sheath 134 in FIG. 30.

In one aspect of the present invention, an implantable stent is provided. The stent includes a plurality of elongate wires braided to form a hollow tubular structure having a tubular wall to define an interior surface and an exterior surface and having opposed open first and second ends, wherein the opposed open first and second ends are atraumatic ends, and further wherein the wires include composite wires to enhance visibility of the wires to provide improved external imaging of the wires in the body. Desirably, the enhanced visibility is enhanced radiopacity and the external imaging is fluoroscopic or x-ray visualization.

The atraumatic ends of the stent are desirably free of any loose wire ends.

The elongate composite wires of the stent may be metallic wires having an outer metallic portion including a first metal and an inner metallic core portion including a second metal, wherein the first metal is different from the second metal. Desirably, the second metal of the inner core includes a radiopaque material selected from gold, barium sulfate, ferritic particles, platinum, platinum-tungsten, palladium, platinum-iridium, rhodium, tantalum or combinations thereof. The first metal of the outer portion may include nitinol.

The stent of this aspect of the present invention desirably may also have wires that terminate at the second end, wherein the wires at the first end are arranged in a series of closed loops with each loop having an apex defined by a bend in one of the wires and having an opposed base defined by crossing of adjacent wires, and further wherein the apex of adjacent closed loops are longitudinally offset from one and the other.

The stent of this aspect of the present invention desirably may also have wires that terminate at the second open end, and adjacently juxtaposed wires are securably joined at the second open end to provide first securably joined regions, wherein at least one of the adjacently juxtaposed stent wires are extended past the first securably joined regions and further wherein the extended and looped wire is securably joined to the proximal pair of wires with second securably joined regions to define closed loop wire ends. Desirably, the wires are securably joined by welding the wired and further wherein the securably joined regions are welds.

The stent of this aspect of the present invention desirably may also have wires that terminate at the second open end, and further wherein adjacently juxtaposed wires at the second open end are securably joined to provide securably joined regions, wherein ends of the terminated wires are smoothed to remove sharp edges from the wire ends. Desirably, the wires are securably joined by welding the wired and further wherein the securably joined regions are welds.

The stent of this aspect of the present invention desirably may also have wires that terminate at the second open end, and adjacently juxtaposed wires are securably joined at the second open end to provide first securably joined regions, wherein at least one of the adjacently juxtaposed stent wires are extended past the first securably joined regions and looped such that the extended end abuts a proximal pair of stent wires; and further wherein the extended and looped wire is securably joined to the proximal pair of wires with second securably joined regions which are longitudinally offset from the first securably joined regions. Desirably, the wires are securably joined by welding the wired and further wherein the securably joined regions are welds. The first and the second welds may have a substantially same longitudinally extending extend. The first and the second welds may have longitudinally extending portions which overlap one and the other.

The stent of this aspect of the present invention may also be partially or fully coated with a polymeric material. The stent may further include hollow tubular graft disposed partially or fully over the interior or the exterior surface. Desirably, the graft is a polymeric material. The polymeric material may be selected from polyester, polypropylene, polyethylene, polyurethane, polynaphthalene, polytetrafluoroethylene, expanded polytetrafluoroethylene, silicone, and combinations thereof.

In another aspect of the present invention, a method for making an implantable stent is provided. The method includes the steps of (i) providing a plurality of elongate wires, wherein the elongate wires include composite wires to enhance visibility of the wires to provide improved external imaging of the wires in the body; and (ii) braiding the wires to form a hollow tubular structure having a tubular wall to define an interior surface and an exterior surface and having opposed open first and second ends, wherein the opposed open first and second ends are atraumatic ends. Desirably, the enhanced visibility is enhanced radiopacity and the external imaging is fluoroscopic or x-ray visualization.

The method this aspect of the present invention may further include the step of arranging the wires at the first end in a series of closed loops with each loop having an apex defined by a bend in one of the wires and having an opposed base defined by crossing of adjacent wires, wherein the apex of adjacent closed loops are longitudinally offset from one and the other.

The method this aspect of the present invention may also further include the steps of terminating the wires at the second end; aligning the wires at the second end into a plurality of mated adjacent wires to define a plurality of juxtaposed regions; and securably joining the mated adjacent wires to one and the other at the juxtaposed regions to define a closed loop at the second end. Desirably, the step of securably joining the wires includes welding the wires.

The method this aspect of the present invention may further include the steps of terminating the wires at the second end to form terminated wire ends; aligning the wires at the second end into a plurality of mated adjacent wires to define a plurality of juxtaposed regions; securably joining the mated adjacent wires to one and the other at the juxtaposed regions to define a plurality of securably joined regions; and smoothing the terminated wire ends by removing sharp edges from the wire ends. Desirably, the step of securably joining the wires includes welding the wires, and further wherein the securably joined regions are welds.

The method this aspect of the present invention may further include the steps of terminating the wires at the second end; aligning the wires at the second end into a plurality of mated adjacent wires to define a plurality of juxtaposed regions; extending at least one of the mated stent wires to provide an extended stent wire; looping the extended stent wire so the extended end abuts a proximal pair of stent wires; securably joining the mated adjacent wires to one and the other at the juxtaposed regions; and securably joining the extended and looped wire to the proximal pair of wires with a pair of longitudinally offset securably joined regions. Desirably, the step of securably joining the wires includes welding the wires, and further wherein the securably joined regions are welds.

In another aspect of the present invention, a stent delivery and deployment system is provided. The system includes a delivery catheter having a distal end; an elongate radially self-expanding stent having a distal end adjacent the distal end of the catheter; an elongate sheath retractably positioned about the stent so as to maintain the stent in a radially compressed delivery condition about the distal end of the catheter; and a retaining band positioned adjacent the distal end of the stent, the retaining band being retractable with the sheath so as to allow longitudinally progressive and radial expansion of the stent upon the retraction of the sheath for deploying the stent. The retaining band may include a radiopaque marker. The band may also be formed of a radiopaque material.

In yet another aspect of the present invention, a method of delivering and deploying an expandable stent includes the steps of disposing a radially expanding stent at a distal end of a delivery catheter; positioning a retractable sheath having a retaining band adjacent a distal end of the stent over the stent so as to maintain the stent in a radially compressed delivery condition; and retracting the sheath and the retaining band with respect to the distal end of the catheter to allow longitudinal progressive expansion of the stent. The sheath and the band are retracted together. The retaining band may include a radiopaque marker or is formed of a radiopaque material. The positioning step may further include the step of positioning the band at the distal end of the stent. Desirably, the stent is a braided stent having opposed first and second atraumatic open ends.

In one aspect of the present invention, a method for making an implantable stent includes the steps of (i) providing a plurality of elongate stent wires; (ii) forming the wires into a hollow tubular structure having opposed first and second open ends; (iii) terminating the wires at the second end to form terminated wire ends; (iii) aligning the wires at the second end into a plurality of mated adjacent wires to define a plurality of juxtaposed regions; (iv) welding the mated adjacent wires to one and the other at the juxtaposed regions to define a plurality of welds; and (v) smoothing the terminated wire ends by removing sharp edges from the wire ends. The step of smoothing the terminated wire ends may further include removing a portion of wire material at the terminated wire end to provide a diagonally extending portion at the wire end; removing a portion of wire material at the terminated wire end to provide a curved portion at the wire end; heating the terminated wire end to partially melt wire material at the wire end; and combinations thereof. Desirably, the step of heating includes passing a laser beam over the terminated wire end.

The method of this aspect of the present invention claim 1 may further include the steps of chemically or electro-chemically removing a portion of the welds; chemically or electro-chemically removing a portion of the terminated wire ends and combinations thereof.

The method of this aspect of the present invention of claim 1 may include forming the tubular structure by braiding the wires, winding the wires, knitting the wires, and combinations thereof.

The method of this aspect of the present invention claim 1 may include a wire including a radiopaque material. The elongate wires may include biocompatible materials selected from the group consisting of nitinol, cobalt-based alloy, stainless steel, platinum, gold, titanium, tantalum, niobium, polymeric materials and combinations thereof, desirably, nitinol. Further, the elongate wires may be composite wires for improved radiopacity, such as wires having an inner core radiopaque material selected from the group consisting of gold, barium sulfate, ferritic particles, platinum, platinum-tungsten, palladium, platinum-iridium, rhodium, tantalum or combinations thereof and an outer portion of nitinol.

In another aspect of the present invention, an implantable stent includes a plurality of wires arranged to form a hollow tubular structure having a tubular wall to define an interior surface and an exterior surface and having opposed open first and second ends, wherein the wires terminate at the second open end and adjacently juxtaposed wires are welded at the second open end with a welding material to provide welds, and further wherein ends of the terminated wires are smoothed to remove sharp edges from the wire ends and to provide a longitudinally extending wire portion at the wire ends. The longitudinally extending wire portion at the wire ends may include a diagonally extending portion at the wire end, may include a curved portion at the wire end, may include partially melt wire material at the wire end, and combinations thereof.

The stent of this aspect of the present invention may include wires including a biocompatible material selected from the group consisting of nitinol, stainless steel, cobalt-based alloy, platinum, gold, titanium, tantalum, niobium, polymeric materials and combinations thereof and an outer portion of nitinol. The weld material and the wire material may be nitinol. The elongate wires have an inner core radiopaque material selected from the group consisting of gold, barium sulfate, ferritic particles, platinum, platinum-tungsten, palladium, platinum-iridium, rhodium, tantalum or combinations thereof and an outer portion of nitinol.

The stent of this aspect of the present invention may include a coated or partially coated stent wherein the stent is coated with a polymeric material. The stent may be is partially or fully covered with a biologically active material which is elutably disposed with the polymeric material.

The stent of this aspect of the present invention may further include a hollow tubular graft disposed over the interior or the exterior surface. The graft may be a polymeric material, such as polyester, polypropylene, polyethylene, polyurethane, polynaphthalene, polytetrafluoroethylene, expanded polytetrafluoroethylene, silicone, and combinations thereof.

Desirably, the stent of this aspect of the present invention is a braided stent.

In another aspect of the resent invention, a method for making an implantable stent including (i) providing a plurality of elongate stent wires; forming the wires into a hollow tubular structure having opposed first and second open ends; terminating the wires at the second end; aligning the wires at the second end into a plurality of mated adjacent wires to define a plurality of juxtaposed regions; and extending at least one of the mated stent wires to provide an extended stent wire; looping the extended stent wire so the extended end abuts a proximal pair of stent wires; welding the mated adjacent wires to one and the other at the juxtaposed regions; and welding the extended and looped wire to the proximal pair of wires with a pair of longitudinally offset welds. The pair of longitudinally offset welds may have a substantially same longitudinally extending extend, may have a portion which overlap one and the other, or combinations thereof.

The step of forming the tubular structure may include braiding the wires, winding the wires, knitting the wires, and combinations thereof. The wire may include a radiopaque material. The elongate wires may include biocompatible materials selected from the group consisting of nitinol, cobalt-based alloy, stainless steel, platinum, gold, titanium, tantalum, niobium, polymeric materials and combinations thereof, desirably nitinol. The elongate wires may be composite wires for improved radiopacity. The elongate wires may have an inner core radiopaque material selected from the group consisting of gold, barium sulfate, ferritic particles, platinum, platinum-tungsten, palladium, platinum-iridium, rhodium, tantalum or combinations and an outer portion of nitinol.

The step of welding may include welding selected from the group consisting of laser welding, electron beam welding resistance welding, tungsten inert gas welding, metal inert gas welding and combinations thereof.

In another aspect of the present invention, an implantable stent includes a plurality of wires arranged to form a hollow tubular structure having a tubular wall to define an interior surface and an exterior surface and having opposed open first and second ends, wherein the wires terminate at the second open end and adjacently juxtaposed wires are welded at the second open end with a welding material to provide first welds, wherein at least one of the adjacently juxtaposed stent wires are extended past the welds and looped such that the extended end abuts a proximal pair of stent wires; and further wherein the extended and looped wire is welded with a welding material to the proximal pair of wires with second welds which are longitudinally offset from the first welds. The first and the second welds may have a substantially same longitudinally extending extend, may have a longitudinally extending portions which overlap one and the other, or combinations thereof.

The wires may include a biocompatible material selected from the group consisting of nitinol, stainless steel, cobalt-based alloy, platinum, gold, titanium, tantalum, niobium, polymeric materials and combinations thereof. The weld material and the wire material may be nitinol. The elongate wires may have an inner core radiopaque material selected from the group consisting of gold, barium sulfate, ferritic particles, platinum, platinum-tungsten, palladium, platinum-iridium, rhodium, tantalum or combinations thereof and an outer portion of nitinol.

The stent may be coated with a polymeric material. The stent may be partially or fully covered with a biologically active material which is elutably disposed with the polymeric material. The stent may further include a hollow tubular graft disposed over the interior or the exterior surface. The graft may be a polymeric material, such as a polymeric material is selected from the group consisting of polyester, polypropylene, polyethylene, polyurethane, polynaphthalene, polytetrafluoroethylene, expanded polytetrafluoroethylene, silicone, and combinations thereof.

Desirably, the stent is a braided stent.

In another aspect of the present invention, an implantable stent includes a plurality of wires arranged to form a hollow tubular structure having a tubular wall to define an interior surface and an exterior surface and having opposed open first and second ends, wherein the wires at the first end are arranged in a series of closed loops with each loop having an apex defined by a bend in one of the wires and having an opposed base defined by crossing of adjacent wires, wherein the apex of adjacent closed loops are longitudinally offset from one and the other. The closed loops may define geometric areas of substantially the same size, may have substantially similar geometric shapes and combinations thereof. The adjacent bases of the closed loops may be longitudinally offset from one and the other, may not be substantially longitudinally offset from one and the other, and combinations thereof.

The loops may have a geometric pattern in a general diamond shape having four corners with the apex forming a top corner, the base forming an opposed bottom corner and opposed side corners defined by crossing of adjacent wires which are different wires from those defining the base corner. The opposed side corners of adjacent closed loops may be longitudinally offset from one and the other, may not be substantially longitudinally offset from one and the other or combinations thereof. Each of the apexes of the closed loops may be longitudinally positioned beyond the opposed corner of any of the closed loops. Each of the apexes may have an area of curvature and adjacent apexes are longitudinally offset by a longitudinal distance where the adjacent apexes of the closed loops are longitudinally positioned within the area of curvature of adjacent loops.

The wires may terminate at the second open end and adjacently juxtaposed wires are welded at the second open end with a welding material to provide first welds, wherein at least one of the adjacently juxtaposed stent wires are extended past the welds and further wherein the extended and looped wire is welded with a welding material to the proximal pair of wires with second welds to define closed loop wire ends. The closed loop wire ends at the second open end may have apexes where the apexes of adjacent closed loop wire ends are longitudinally offset from one and the other. The second welds may be longitudinally offset from the first welds. The ends of the terminated wires may be smoothed by removing sharp edges from the wire ends.

The wires may include a biocompatible material selected from the group consisting of nitinol, stainless steel, cobalt-based alloy, platinum, gold, titanium, tantalum, niobium, polymeric materials and combinations thereof and an outer portion of nitinol. The s weld material and the wire material may be nitinol. The elongate wires may have an inner core radiopaque material selected from the group consisting of gold, barium sulfate, ferritic particles, platinum, platinum-tungsten, palladium, platinum-iridium, rhodium, tantalum or combinations thereof and an outer portion of nitinol.

The stent may be coated with a polymeric material. The stent may be partially or fully covered with a biologically active material which is elutably disposed with the polymeric material. A hollow tubular graft may be disposed over the interior or the exterior surface. The graft may be a polymeric material, such as a polymeric material is selected from the group consisting of polyester, polypropylene, polyethylene, polyurethane, polynaphthalene, polytetrafluoroethylene, expanded polytetrafluoroethylene, silicone, and combinations thereof.

Desirably, the stent may be a braided stent.

In another aspect of the present invention, a method for making an implantable stent includes (i) providing a plurality of elongate stent wires; and (ii) forming the wires into a hollow tubular structure having opposed first and second open ends, wherein the wires at the first end are arranged in a series of closed loops with each loop having an apex defined by a bend in one of the wires and having an opposed base defined by crossing of adjacent wires, wherein the apex of adjacent closed loops are longitudinally offset from one and the other. The method may further include the steps of (i) terminating the wires at the second end; (ii) aligning the wires at the second end into a plurality of mated adjacent wires to define a plurality of juxtaposed regions; and (iii) welding the mated adjacent wires to one and the other at the juxtaposed regions to define a closed loop at the second end. The adjacent closed loops at the second end may be longitudinally staggered from one and the other. The step of forming the tubular structure may include braiding the wires, winding the wires, knitting the wires, and combinations thereof.

The wire may include a radiopaque material. The elongate wires may include biocompatible materials selected from the group consisting of nitinol, cobalt-based alloy, stainless steel, platinum, gold, titanium, tantalum, niobium, polymeric materials and combinations thereof. Desirably, the elongate wires may include nitinol. The elongate wires may be composite wires for improved radiopacity. The elongate wires may have an inner core radiopaque material selected from the group consisting of gold, barium sulfate, ferritic particles, platinum, platinum-tungsten, palladium, platinum-iridium, rhodium, tantalum or combinations thereof and an outer portion of nitinol.

In another aspect of the present invention, a stent delivery and deployment system includes (i) a delivery catheter having a distal end; (ii) an elongate radially self-expanding stent having a distal end adjacent the distal end of the catheter; (iii) an elongate sheath retractably positioned about the stent so as to maintain the stent in a radially compressed delivery condition about the distal end of the catheter; and (iv) a retaining band positioned adjacent the distal end of the stent, the retaining band being retractable with the sheath so as to allow longitudinally progressive and radial expansion of the stent upon the retraction of the sheath for deploying the stent. The retaining band may be positioned at the distal end of the stent, may be positioned between the stent and the sheath, may be positioned external to the sheath and combinations thereof. The retaining band may include a radiopaque marker. The band may be imbedded into the sheath. The band may be formed of a radiopaque material.

In another aspect of the present invention, a method of delivering and deploying an expandable stent includes the steps of (i) disposing a radially expanding stent at a distal end of a delivery catheter; (ii) positioning a retractable sheath having a retaining band adjacent a distal end of the stent over the stent so as to maintain the stent in a radially compressed delivery condition; and (iii) retracting the sheath and the retaining band with respect to the distal end of the catheter to allow longitudinal progressive expansion of the stent. The sheath and the band may be retracted together. The band may be imbedded into the sheath. The retaining band may include a radiopaque marker. The positioning step may include positioning the band at the distal end of the stent.

In another aspect of the present invention, a system for locating a stent for delivery and deployment at an intraluminal site includes (i) a delivery catheter having a distal end; (ii) an elongate deployable stent mounted to the distal end of the catheter; and (iii) a radiopaque marker on the distal end of the catheter; the stent being mounted on the distal end to overlie the marker. The stent may be a distensible stent. The marker may be positioned adjacent one end of the stent. The stent may have a distal end and a proximal end and the marker may positioned adjacent the proximal end.

A method of deploying a stent at a damaged vessel site includes the step of (i) providing a catheter having a delivery end and a radiopaque marker adjacent there to; (ii) positioning an expandable stent on the delivery end so as to overlie the marker; (iii) placing the marker at a location proximal to the damaged vessel site; and (iv) allowing the stent to expand across the damaged vessel site. The marker may be placed before the damaged vessel site to ensure positioning of the expanded stent across the damaged vessel site.

A stent delivery and deployment system may include (i) a delivery catheter having a distal end; (ii) an elongate radially self-expanding stent having a distal end adjacent the distal end of the catheter, the stent including a plurality of wires arranged to form a hollow tubular structure having a tubular wall to define an interior surface and an exterior surface and having opposed open first and second ends, wherein the wires terminate at the second open end and adjacently juxtaposed wires are welded at the second open end with a welding material to provide welds, and further wherein ends of the terminated wires are smoothed to remove sharp edges from the wire ends and to provide a longitudinally extending wire portion at the wire ends; (iii) an elongate sheath retractably positioned about the stent so as to maintain the stent in a radially compressed delivery condition about the distal end of the catheter; and (iv) a retaining band positioned adjacent the distal end of the stent, the retaining band being retractable with the sheath so as to allow longitudinally progressive and radial expansion of the stent upon the retraction of the sheath for deploying the stent.

A stent delivery and deployment system may also include (i) a delivery catheter having a distal end; (ii) an elongate radially self-expanding stent having a distal end adjacent the distal end of the catheter, the stent including a plurality of wires arranged to form a hollow tubular structure having a tubular wall to define an interior surface and an exterior surface and having opposed open first and second ends, wherein the wires terminate at the second open end and adjacently juxtaposed wires are welded at the second open end with a welding material to provide first welds, wherein at least one of the adjacently juxtaposed stent wires are extended past the welds and looped such that the extended end abuts a proximal pair of stent wires; and further wherein the extended and looped wire is welded with a welding material to the proximal pair of wires with second welds which are longitudinally offset from the first welds; (iii) an elongate sheath retractably positioned about the stent so as to maintain the stent in a radially compressed delivery condition about the distal end of the catheter; and (iv) a retaining band positioned adjacent the distal end of the stent, the retaining band being retractable with the sheath so as to allow longitudinally progressive and radial expansion of the stent upon the retraction of the sheath for deploying the stent.

A stent delivery and deployment system may include (i) a delivery catheter having a distal end; (ii) an elongate radially self-expanding stent having a distal end adjacent the distal end of the catheter, the stent including a plurality of wires arranged to form a hollow tubular structure having a tubular wall to define an interior surface and an exterior surface and having opposed open first and second ends, wherein the wires at the first end are arranged in a series of closed loops with each loop having an apex defined by a bend in one of the wires and having an opposed base defined by crossing of adjacent wires, wherein the apex of adjacent closed loops are longitudinally offset from one and the other; (iii) an elongate sheath retractably positioned about the stent so as to maintain the stent in a radially compressed delivery condition about the distal end of the catheter; and (iv) a retaining band positioned adjacent the distal end of the stent, the retaining band being retractable with the sheath so as to allow longitudinally progressive and radial expansion of the stent upon the retraction of the sheath for deploying the stent.

The invention being thus described, it will now be evident to those skilled in the art that the same may be varied in many ways. Such variations are not to be regarded as a departure from the spirit and scope of the invention and all such modifications are intended to be included within the scope of the following claims.

What is claimed is:

1. An implantable stent comprising:
    a plurality of elongate wires braided to form a hollow tubular structure having a tubular wall to define an interior surface and an exterior surface and having opposed open first and second ends;
    wherein said opposed open first and second ends are atraumatic ends,
    wherein said wires terminate at said second end;
    wherein said wires at said first end are arranged in a series of closed loops with each loop having an apex defined by a bend in one of said wires and having an opposed base defined by crossing of adjacent wires; and
    further wherein said apex of adjacent closed loops are longitudinally offset from one and the other.

2. The stent of claim 1, wherein said wires comprise composite wires to enhance visibility of the wires to provide improved external imaging of the wires in the body.

3. The stent of claim 2, wherein the enhanced visibility is enhanced radiopacity and the external imaging is fluoroscopic or x-ray visualization.

4. The stent of claim 2, wherein said elongate composite wires are metallic wires having an outer metallic portion comprising a first metal and an inner metallic core portion comprising a second metal, wherein said first metal is different from said second metal.

5. The stent of claim 4, wherein said second metal of said inner core comprises a radiopaque material selected from the group consisting of gold, barium sulfate, ferritic particles, platinum, platinum-tungsten, palladium, platinum-iridium, rhodium, tantalum or combinations thereof.

6. The stent of claim 4, wherein said first metal of said outer portion comprises nitinol.

7. The stent of claim 1, wherein said atraumatic ends are free of any loose wire ends.

8. The stent of claim 1, wherein adjacently juxtaposed wires are securably joined at said second open end to provide first securably joined regions, wherein at least one of said adjacently juxtaposed stent wires are extended past said first securably joined regions and further wherein said extended and looped wire is securably joined to said proximal pair of wires with second securably joined regions to define closed loop wire ends.

9. The stent of claim 8, wherein said wires are securably joined by welding said wires and further wherein said securably joined regions are welds.

10. The stent of claim 1, wherein adjacently juxtaposed wires at said second open end are securably joined to provide securably joined regions, wherein ends of said terminated wires are smoothed to remove sharp edges from said wire ends.

11. The stent of claim 10, wherein said wires are securably joined by welding said wires and further wherein said securably joined regions are welds.

12. An implantable stent comprising:
    a plurality of elongate wires braided to form a hollow tubular structure having a tubular wall to define an interior surface and an exterior surface and having opposed open first and second ends;
    wherein said opposed open first and second ends are atraumatic ends;
    wherein said wires terminate at said second open end, and adjacently juxtaposed wires are securably joined at said second open end to provide first securably joined regions;
    wherein at least one of said adjacently juxtaposed stent wires are extended past said first securably joined regions and looped such that the extended end abuts a proximal pair of stent wires; and
    further wherein said extended and looped wire is securably joined to said proximal pair of wires with second securably joined regions which are longitudinally offset from said first securably joined regions.

13. The stent of claim 12, wherein said wires are securably joined by welding said wires and further wherein said securably joined regions are welds.

14. The stent of claim 13, wherein said first and said second welds have a substantially same longitudinally extending extend.

15. The stent of claim 13, wherein said first and said second welds have a longitudinally extending portions which overlap one and the other.

16. The stent of claim 1, wherein said stent is partially or fully coated with a polymeric material.

17. The stent of claim 1, further comprising a hollow tubular graft disposed partially or fully over said interior or said exterior surface.

18. The stent of claim 17, wherein said graft is a polymeric material.

19. The stent of claim 18, wherein said polymeric material is selected from the group consisting of polyester, polypropylene, polyethylene, polyurethane, polynaphthalene, polytetrafluoroethylene, expanded polytetrafluoroethylene, silicone, and combinations thereof.

20. The stent of claim 12, wherein said wires comprise composite wires to enhance visibility of the wires to provide improved external imaging of the wires in the body.

* * * * *